United States Patent
Sengun et al.

(10) Patent No.: US 8,308,814 B2
(45) Date of Patent: Nov. 13, 2012

(54) METHODS AND DEVICES FOR PREPARING AND IMPLANTING TISSUE SCAFFOLDS

(75) Inventors: Mehmet Z. Sengun, Braintree, MA (US); Kristian DiMatteo, Waltham, MA (US)

(73) Assignee: DePuy Mitek, Inc., Raynham, MA (US)

( * ) Notice: Subject to any disclaimer, the term of this patent is extended or adjusted under 35 U.S.C. 154(b) by 553 days.

(21) Appl. No.: 12/412,492

(22) Filed: Mar. 27, 2009

(65) Prior Publication Data

US 2010/0249758 A1    Sep. 30, 2010

(51) Int. Cl.
*A61F 2/02*    (2006.01)
(52) U.S. Cl. .................................................. 623/23.72
(58) Field of Classification Search ................. 606/151, 606/213, 232, 79–85, 166–180; 623/23.72; 128/898; 600/37; 33/18.1
See application file for complete search history.

(56) References Cited

U.S. PATENT DOCUMENTS

| | | | |
|---|---|---|---|
| 5,306,311 A | 4/1994 | Stone et al. | |
| 5,484,403 A | 1/1996 | Yoakum et al. | |
| 5,632,745 A | 5/1997 | Schwartz | |
| 5,690,674 A | 11/1997 | Diaz | |
| 5,769,899 A | 6/1998 | Schwartz et al. | |
| 5,876,440 A | 3/1999 | Feingold | |
| 5,885,293 A * | 3/1999 | McDevitt | 606/80 |
| 6,001,107 A | 12/1999 | Feingold | |
| 6,143,000 A | 11/2000 | Feingold | |
| 6,179,840 B1 | 1/2001 | Bowman | |
| 6,251,143 B1 | 6/2001 | Schwartz et al. | |
| 6,364,884 B1 | 4/2002 | Bowman et al. | |
| 6,402,766 B2 | 6/2002 | Bowman et al. | |
| 6,423,073 B2 | 7/2002 | Bowman | |
| 6,436,068 B1 | 8/2002 | Bardy | |
| 6,436,110 B2 | 8/2002 | Bowman et al. | |
| 6,447,517 B1 | 9/2002 | Bowman | |
| 6,468,314 B2 | 10/2002 | Schwartz et al. | |
| 6,497,707 B1 | 12/2002 | Bowman et al. | |
| 6,610,067 B2 | 8/2003 | Tallarida et al. | |
| 6,669,706 B2 | 12/2003 | Schmitt et al. | |
| D491,807 S | 6/2004 | Cauldwell et al. | |
| D494,063 S | 8/2004 | Cauldwell et al. | |
| 6,852,125 B2 | 2/2005 | Simon et al. | |
| 6,852,330 B2 | 2/2005 | Bowman et al. | |
| 6,858,042 B2 | 2/2005 | Nadler et al. | |
| 6,884,428 B2 | 4/2005 | Binette et al. | |
| 7,115,100 B2 | 10/2006 | McRury et al. | |

(Continued)

FOREIGN PATENT DOCUMENTS

EP    1070487 A2    1/2001

(Continued)

OTHER PUBLICATIONS

Extended European Search Report in EP App. No. 10250619.3 dated Dec. 21, 2010 (12 pages).

(Continued)

*Primary Examiner* — Melanie Tyson

(57) ABSTRACT

Methods and devices are provided for preparing and implanting tissue scaffolds. Various embodiments of scribing tools are provided that are configured to mark one or more predetermined shapes around a defect site in tissue. The shape or shapes marked in tissue can be used to cut a tissue scaffold having a shape that matches the shape or shapes marked in tissue. In one embodiment, the scribing tool used to mark a shape in tissue can also be used to cut the tissue scaffold.

20 Claims, 10 Drawing Sheets

U.S. PATENT DOCUMENTS

| | | | |
|---|---|---|---|
| 7,160,326 | B2 | 1/2007 | Ball |
| 7,163,563 | B2 | 1/2007 | Schwartz et al. |
| 7,235,107 | B2 * | 6/2007 | Evans et al. ............ 623/23.51 |
| 7,571,729 | B2 * | 8/2009 | Saadat et al. ............ 128/898 |
| 2001/0010023 | A1 | 7/2001 | Schwartz et al. |
| 2002/0052628 | A1 | 5/2002 | Bowman |
| 2002/0095157 | A1 | 7/2002 | Bowman |
| 2002/0119177 | A1 | 8/2002 | Bowman et al. |
| 2002/0127265 | A1 | 9/2002 | Bowman et al. |
| 2002/0147498 | A1 | 10/2002 | Tallarida et al. |
| 2002/0169465 | A1 | 11/2002 | Bowman et al. |
| 2003/0036801 | A1 | 2/2003 | Schwartz et al. |
| 2003/0055502 | A1 | 3/2003 | Lang et al. |
| 2003/0147935 | A1 | 8/2003 | Binette et al. |
| 2003/0236573 | A1 | 12/2003 | Evans et al. |
| 2004/0015170 | A1 | 1/2004 | Tallarida et al. |
| 2004/0078077 | A1 | 4/2004 | Binette et al. |
| 2004/0078090 | A1 | 4/2004 | Binette et al. |
| 2004/0138664 | A1 | 7/2004 | Bowman |
| 2004/0147927 | A1 | 7/2004 | Tsougarakis et al. |
| 2004/0175408 | A1 | 9/2004 | Chun et al. |
| 2004/0193071 | A1 | 9/2004 | Binette et al. |
| 2004/0193154 | A1 | 9/2004 | Leatherbury et al. |
| 2004/0267277 | A1 | 12/2004 | Zannis et al. |
| 2004/0267362 | A1 | 12/2004 | Hwang et al. |
| 2005/0038520 | A1 | 2/2005 | Binette et al. |
| 2005/0054595 | A1 | 3/2005 | Binette et al. |
| 2005/0059905 | A1 | 3/2005 | Boock et al. |
| 2005/0113736 | A1 | 5/2005 | Orr et al. |
| 2005/0113937 | A1 | 5/2005 | Binette et al. |
| 2005/0113938 | A1 | 5/2005 | Jamiolkowski et al. |
| 2005/0125077 | A1 | 6/2005 | Harmon et al. |
| 2005/0137600 | A1 | 6/2005 | Jacobs et al. |
| 2005/0154399 | A1 | 7/2005 | Weber et al. |
| 2005/0177249 | A1 | 8/2005 | Kladakis et al. |
| 2005/0209610 | A1 * | 9/2005 | Carrison ............ 606/114 |
| 2005/0222687 | A1 | 10/2005 | Vunjak-Novakovic et al. |
| 2005/0232967 | A1 | 10/2005 | Kladakis et al. |
| 2005/0234549 | A1 | 10/2005 | Kladakis et al. |
| 2006/0173539 | A1 | 8/2006 | Shiuey |
| 2006/0178748 | A1 | 8/2006 | Dinger et al. |
| 2006/0241568 | A1 | 10/2006 | Roger |
| 2006/0241756 | A1 | 10/2006 | Fritz et al. |
| 2006/0257379 | A1 * | 11/2006 | Giordano et al. ............ 424/93.7 |
| 2006/0292131 | A1 | 12/2006 | Binette et al. |
| 2006/0293760 | A1 | 12/2006 | DeDeyne |
| 2007/0031470 | A1 | 2/2007 | Kladakis et al. |
| 2007/0038299 | A1 | 2/2007 | Stone et al. |
| 2007/0043376 | A1 | 2/2007 | Leatherbury et al. |
| 2007/0073394 | A1 | 3/2007 | Seedhom et al. |
| 2008/0181954 | A1 | 7/2008 | Binette et al. |
| 2008/0234715 | A1 | 9/2008 | Pesce et al. |
| 2010/0249801 | A1 | 9/2010 | Sengun et al. |

FOREIGN PATENT DOCUMENTS

| | | |
|---|---|---|
| GB | 2452987 A | 3/2009 |
| WO | WO-03028535 A2 | 4/2003 |

OTHER PUBLICATIONS

Partial European Search Report in EP App. No. 10250619.3 dated Jul. 5, 2010 (5 pages).

Office Action in U.S. Appl. No. 12/412,499 dated Dec. 23, 2011.

European Search Report and Written Opinion in EP App. No. 11173980.1 dated Sep. 12, 2011 (6 pages).

* cited by examiner

METHODS AND DEVICES FOR PREPARING AND IMPLANTING TISSUE SCAFFOLDS

FIELD OF THE INVENTION

The present invention relates to methods and devices for preparing and implanting tissue scaffolds.

BACKGROUND OF THE INVENTION

Injuries to soft tissue, such as cartilage, skin, muscle, bone, tendon, and ligament, frequently require surgical intervention to repair the damage and facilitate healing. Such surgical repairs can include suturing or otherwise repairing the damaged tissue with known medical devices, augmenting the damaged tissue with other tissue, using an implant, a graft, or any combination of these techniques.

One common tissue injury involves damage to cartilage, which is a non-vascular, resilient, flexible connective tissue. Cartilage typically acts as a "shock-absorber" at articulating joints, but some types of cartilage provide support to tubular structures, such as for example, the larynx, air passages, and the ears. In general, cartilage tissue is comprised of cartilage cells, known as chondrocytes, located in an extracellular matrix, which contains collagen, a structural scaffold, and aggrecan, a space-filling proteoglycan. Several types of cartilage can be found in the body, including hyaline cartilage, fibrocartilage, and elastic cartilage. Hyaline cartilage can appear in the body as distinct pieces, or alternatively, this type of cartilage can be found fused to the articular ends of bones. Hyaline cartilage is generally found in the body as articular cartilage, costal cartilage, and temporary cartilage (i.e., cartilage that is ultimately converted to bone through the process of ossification). Fibrocartilage is a transitional tissue that is typically located between tendon and bone, bone and bone, and/or hyaline cartilage and hyaline cartilage. Elastic cartilage, which contains elastic fibers distributed throughout the extracellular matrix, is typically found in the epiglottis, the ears, and the nose.

One common example of hyaline cartilage injury is a focal articular cartilage defect in the knee. A strong impact to the joint can result in the partial removal of a cartilage fragment of various size and shape or sufficiently damage the extracellular matrix of the cartilage to cause degeneration of cartilage. If left untreated, damaged articular cartilage can restrict joint function, cause debilitating pain and may result in long term chronic diseases such as osteoarthritis, a disease characterized by cartilage breakdown and unfavorable changes in the underlying bone. As injuries to the articular cartilage tissue generally do not heal on their own, surgical intervention is often necessary to repair symptomatic lesions. The current modality of treatment consists of lavage, removal of partially or completely unattached tissue fragments. In addition, the surgeon will often use a variety of methods such as abrasion, drilling, or microfractures, to induce bleeding into the cartilage defect and formation of a clot. It is believed that the cells coming from the marrow will form a scar-like tissue that is fibrocartilaginous in nature and can only provide temporary relief to some symptoms. Unfortunately, the repair tissue does not have the same mechanical properties as hyaline cartilage and therefore degrades faster over time as a consequence of wear. Patients typically require a secondary procedure to alleviate symptoms.

More recently, experimental approaches involving the implantation of autologous chondrocytes have been used with increasing frequency. The chondrocytes are obtained by harvesting a piece of cartilage from a patient using a biopsy and then cells are extracted from the tissue sample and cultured to the appropriate numbers in the laboratory. The expanded chondrocytes are then provided to the surgeon in the form of a cell suspension or pre-loaded onto a synthetic or natural biodegradable, biocompatible scaffold for placement into the cartilage defect site. Sometimes, these living cells are placed in a three-dimensional natural or synthetic scaffold or matrix, and are kept under tissue specific culture conditions to create a transplantable function tissue replacement. If provided with the appropriate conditions and signals, the cells will proliferate, differentiate, and secrete various matrix molecules to create an actual living tissue that can be used as a replacement tissue to be implanted back into the defect site in the patient.

Other techniques for repairing damaged cartilage employ cells other than chondrocytes to produce the desired hyaline-like tissue. Stem or progenitor cells, such as the cells within fatty tissue, muscle, or bone marrow, have the potential to regenerate bone and/or cartilage in a patient. Stem cells can be from that patient, i.e., autogeneic, or from another patient, i.e., allogeneic. These progenitor cells in addition to other cells, such as cells from the synovium, are thought to regenerate cartilage tissue when placed in an environment favorable for inducing cartilage formation.

Other surgical techniques for the surgical treatment of damaged tissue include the use of surgical implants, scaffolds, or matrices. Various surgical implants have been used in surgical procedures to help regenerate cartilage without the use of cells. For example, implants can be created consisting of porous biodegradable, biocompatible polymeric matrices. Other examples include matrices derived from biopolymers such as hyaluronic acid, collagen, and fibrin. These implants are often used in conjunction with marrow stimulation techniques, such as microfracture, such that the marrow can provide the cells as well as other stimulants that will help to regenerate cartilage.

Before an implant can be placed into the patient, preparations must be made to both the defect site and the implant to ensure good integration of the implant with the cartilage surrounding the defect. The patient must be prepared by clearing the degenerate or damaged tissue from the defect site. Particularly in arthroscopic procedures where access to the surgical site is limited, clearing space at the defect site can be difficult and time consuming in attempts to minimize any trauma to the neighboring healthy cartilage and/or subchondral bone, i.e., the bone underlying the defect. The implant must also be prepared by sizing it from its laboratory-created size to match the cleared defect space in the patient. Because the implant cannot be appropriately sized until the space at the defect site in the patient has been formed and its size can be identified, the implant has to be prepared for implantation ad hoc during the surgical procedure. Errors in sizing the implant during the stress of surgery can prolong the surgical procedure and can result in repeated resizing of the tissue replacement to an acceptable size. In some cases attempts to size the implant can result in no appropriately sized implant if it has been cut to one or more unusable sizes. An unusable implant can necessitate creation of another implant in another expensive, time-consuming, and medically intrusive process followed by another attempt at implantation in the patient.

Accordingly, there remains a need for methods and devices for preparing a defect site in a patient and for preparing and placing an implant into the patient.

SUMMARY OF THE INVENTION

The present invention generally provides methods and devices for preparing and implanting tissue scaffolds. In one embodiment, a surgical device is provided that includes an inner shaft having a distal end with a cartilage-engaging element formed thereon, and an outer shaft slidably and rotatably disposed over the inner shaft. The outer shaft has a scribing element formed on a distal end thereof and is configured to form a circular mark in tissue when the outer shaft is rotated relative to the inner shaft. The device can have any number of variations. For example, the outer shaft can have an arm extending radially outward from a distal end thereof at an angle relative to a longitudinal axis of the outer shaft. The scribing element can be formed on a distal end of the arm. For another example, the cartilage-engaging element can include first and second spikes formed on the distal end of the inner shaft. For yet another example, the angle can be in the range of about 20° to 70°. For yet another example, the device can include a handle formed on a proximal end of the outer shaft and/or a handle formed on a proximal end of the inner shaft.

In another aspect, a tissue repair kit is provided. In one embodiment, a tissue repair kit includes a scribing device having a handle, an elongate shaft extending from the handle, and a scribing element formed on a distal end of the elongate shaft. The scribing element extends along an axis that is offset from a longitudinal axis of the elongate shaft, and the scribing element has a distal-most scribing edge that is curved such that rotation of the scribing device about the longitudinal axis of the elongate shaft is effective to cause the scribing edge to form a circular mark in tissue. The kit can also include a biocompatible tissue repair scaffold configured to be implanted in a defect site in tissue.

In another embodiment, a tissue repair kit includes a scribing tool configured to form in tissue a circular mark having a predetermined diameter, and a cutting template device having first and second portions slidably coupled to one another. The first and second portions have a first position in which the first and second portions define a circular cut-out formed therebetween and have a diameter that corresponds to the predetermined diameter. The first and second portions also have an expanded position in which the first and second portions define an oblong cut-out formed therebetween and having a major axis length that is adjustable. The kit can have any number of variations. For example, the first and second portions in the expanded position can define a plurality of oblong cut-outs formed therebetween, each of the plurality of oblong cut-outs having a major axis length that is adjustable. For another example, the first and second portions in the first position can define a plurality of circular cut-outs formed therebetween, each of the plurality of circular cut-outs having a different diameter. In some embodiments, the kit can also include a plurality of scribing tools, each of the plurality of scribing tools configured to form in tissue a circular mark having a predetermined diameter corresponding to one of the diameters of the plurality of circular cut-outs.

In another aspect, a surgical method is provided. In one embodiment, a surgical method includes advancing a surgical device into a body of a patient to position a distal scribing tip of the device at a defect site in tissue, rotating the surgical device about a central longitudinal axis of the surgical device such that the distal scribing tip rotates to form a circular mark in tissue around the defect site, removing the tissue within the circular mark to form a circular cavity in the tissue, cutting a biocompatible tissue repair scaffold to have a circular shape that corresponds to the circular mark formed in the tissue, and implanting the biocompatible tissue repair scaffold in the circular cavity in the tissue. The method can have any number of variations. For example, the surgical device can be inserted through an opening in tissue, and the circular mark can have a diameter that is greater than a diameter of the opening. For another example, the circular mark can have a diameter in the range of about 5 to 40 mm. For yet another example, the biocompatible tissue repair scaffold can have a viable tissue disposed thereon. For still another example, rotating the surgical device can include rotating an outer member having the distal scribing tip formed thereon relative to an inner member that engages bone underlying the tissue.

In another embodiment, a surgical method includes rotating a scribing device about a longitudinal axis of the scribing device to form a first substantially circular mark in tissue at a defect site, rotating a scribing device about a longitudinal axis of the scribing device to form a second substantially circular mark in the tissue at the defect site, and removing tissue within the first and second substantially circular marks to remove a defect in the tissue. The second substantially circular mark partially overlaps the first substantially circular mark. The method can vary in any number of ways. For example, the method can include forming at least one linear mark in the tissue that extends between an outer edge of the first substantially circular mark and an outer edge of the second substantially circular mark. For another example, the method can include first and second linear marks in the tissue, each linear mark being tangent to the first and second substantially circular marks such that the first and second substantially circular marks and the first and second linear marks form an oblong mark in the tissue. For yet another example, the first substantially circular mark can have a diameter that differs from a diameter of the second substantially circular mark. For still another example, a first scribing device can be used to form the first substantially circular mark, and a second scribing device can be used to form the second substantially circular mark. The method can also include removing tissue inside the first and second substantially circular marks to form a cavity in the tissue, and implanting a biocompatible tissue repair scaffold in the cavity in the tissue. In some embodiments, prior to implanting the biocompatible tissue repair scaffold, the method can include measuring a maximum length of the first and second substantially circular marks formed in the tissue, and cutting the biocompatible tissue repair scaffold to have a size and shape that corresponds to a size and shape of the cavity in the tissue.

In yet another embodiment, a surgical method includes measuring a length of an oblong mark formed in tissue, slidably moving first and second portions of a template tool to form a cut-out between the first and second portions that has a length that corresponds to the measured length of the oblong mark formed in the tissue, and using the cut-out to form a tissue repair scaffold having a size and shape that corresponds to the oblong mark formed in the tissue. The method can also include implanting the tissue repair scaffold in the oblong mark in the tissue. In one embodiment, the mark can be formed using a scribing tool configured to form in tissue a circular mark having a predetermined diameter. In some embodiments, slidably moving first and second portions of a template tool can include moving the first and second portions from a first position defining a first shape having a diameter equal to the predetermined diameter to an expanded position defining a second shape that has a length that corresponds to the measured length of the oblong mark formed in the tissue.

In still another embodiment, a surgical method includes advancing a transparent film through a passageway extending through tissue and into a body cavity, positioning the film over a defect in a tissue surface in the body cavity, comparing a shape of the film to a shape of the defect, removing the film from the patient, cutting the film to have a shape that substantially corresponds to the shape of the defect, and using the cut film shape as a template to cut a tissue repair scaffold such that the tissue repair scaffold has a shape that substantially corresponds to the shape of the defect. The film can have a folded configuration when disposed within the passageway, and it can open to a planar configuration upon passage out of the passageway and into the body cavity. The method can vary in any number of ways. For example, the method can include, prior to advancing a transparent film through a passageway, selecting a transparent film from one of a plurality of transparent films having predefined different shapes. For another example, the method can include, prior to using the cut film shape as a template to cut a tissue repair scaffold, repeating the steps of advancing, positioning, comparing, removing, and cutting.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
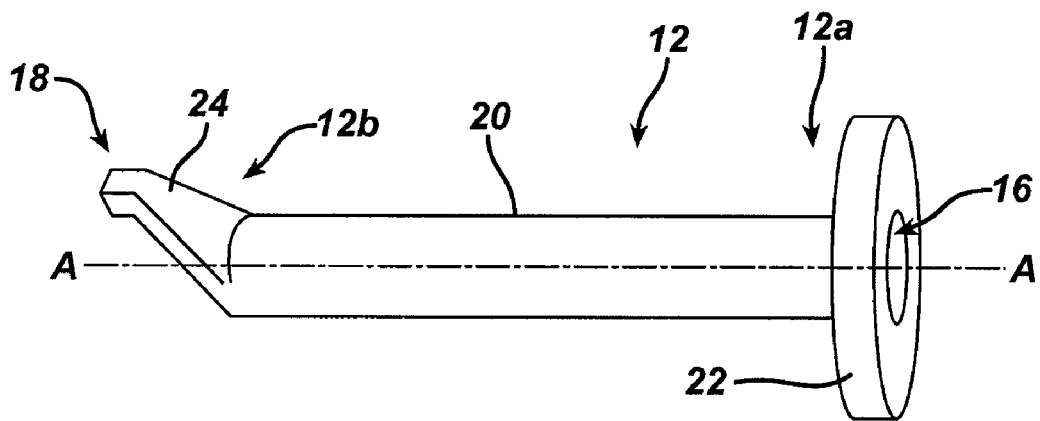
FIG. 1 is a perspective view of one embodiment of an outer shaft of a scribing tool having a distal scribing arm.
Figure 2:
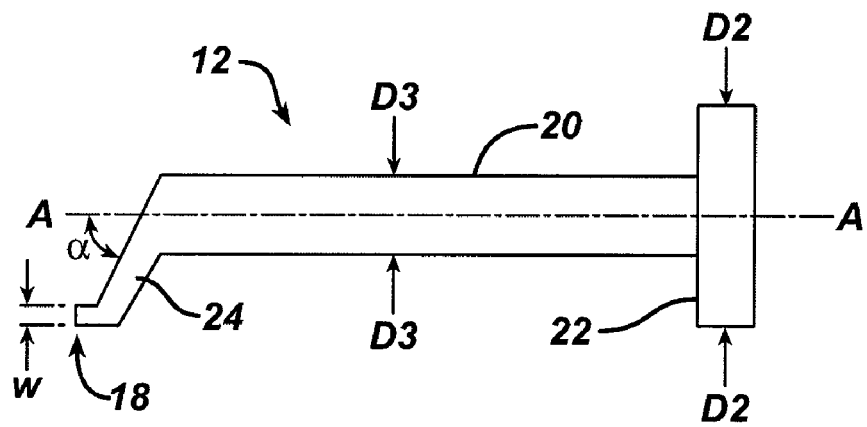
FIG. 2 is a side view of the outer shaft of FIG. 1.
Figure 3:
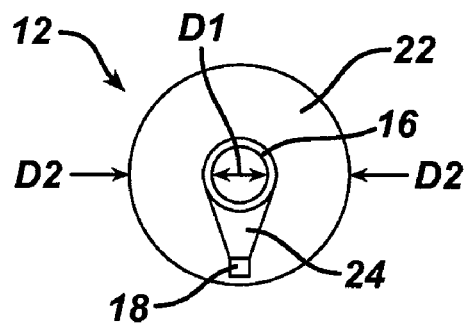
FIG. 3 is a distal end view of the outer shaft of FIG. 1.
Figure 4:
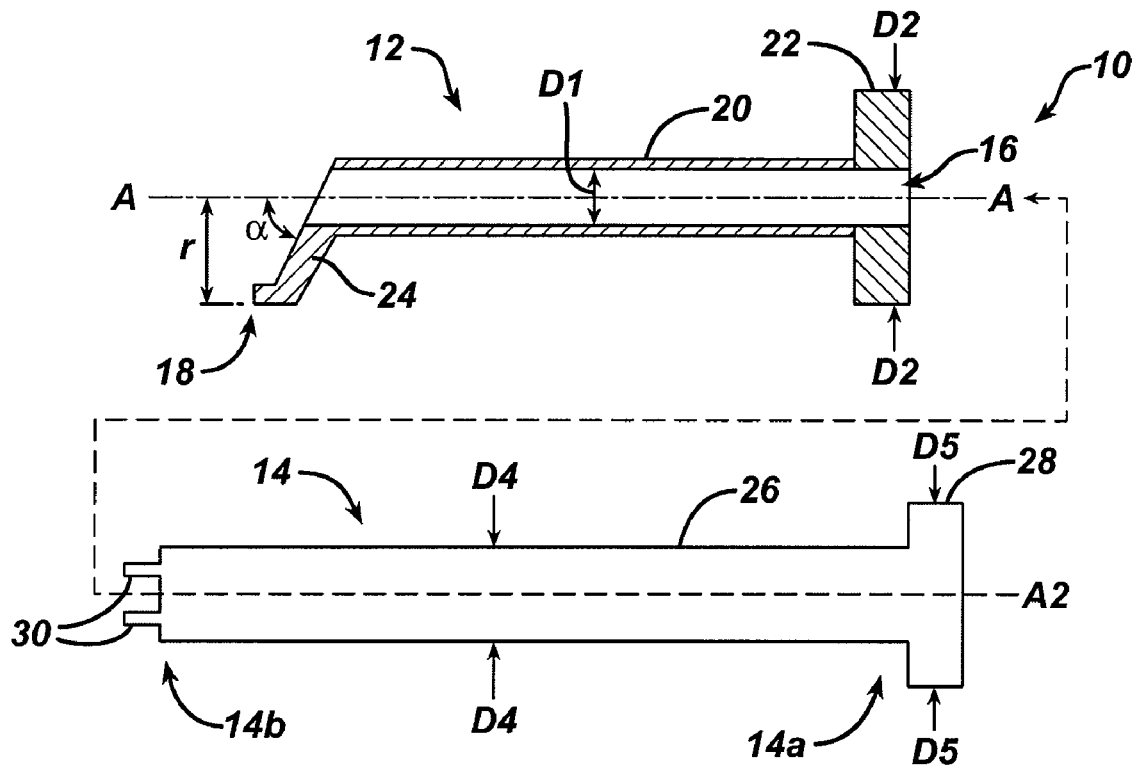
FIG. 4 is a cross-sectional side view of the outer shaft of FIG. 1 and a side view of an inner shaft configured to be disposed in a passageway extending through the outer shaft.
Figure 5:
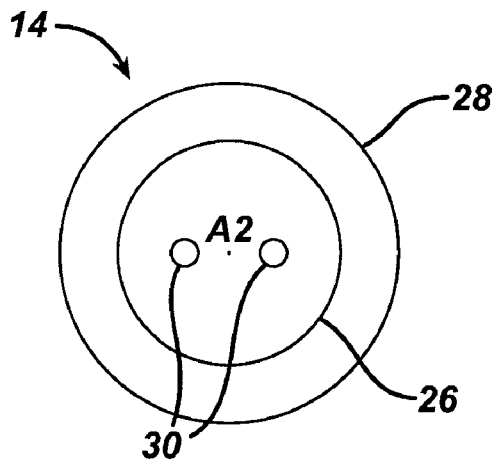
FIG. 5 is a distal end view of the inner shaft of FIG. 4.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides various methods and devices for preparing and implanting tissue replacements. In general, various tools and techniques are disclosed for marking, e.g., scribing or scoring, one or more predetermined shapes, e.g., circles, ovals, oblong shapes, etc., around a defect site in tissue, e.g., cartilage. The marked tissue within the predetermined shape or shapes, i.e., the defective tissue, can be removed to form a cavity in the tissue. Since the shape of the cavity is known because the shape or shapes marked are predetermined, a tissue scaffold can be cut having a shape and size that matches the shape and size of the cavity, thereby providing a scaffold that fills the entire cavity in the tissue.

Various other methods and devices are also provided for determining the shape and size of a cavity in tissue, and for preparing a tissue scaffold having a shape and size that matches the shape and size of the cavity.

A person skilled in the art will appreciate that the term "tissue" as used herein is intended to encompass a variety of materials, e.g., cartilage, organs, and any other material that can be repaired using a tissue scaffold, and that the term "cartilage" as used herein can refer to any type of cartilage, e.g., hyaline cartilage, fibrocartilage, and elastic cartilage. A person skilled in the art will also appreciate that the term "defect site" as used herein is intended to encompass a current or former location in tissue that is damaged, unhealthy, or is otherwise undesirable and intended for repair with a tissue replacement. A person skilled in the art will also appreciate that the term "tissue replacement," "implant," "scaffold," or "matrix" as used herein is intended to encompass any surgically safe implant that is configured to be implanted in a patient to allow for tissue repair and regrowth.

A person skilled in the art will also appreciate that while the methods and devices are described in connection with minimally invasive arthroscopic procedures in which surgical devices are introduced percutaneously into a body cavity through a small opening formed in a patient, the methods and devices disclosed herein can be used in numerous surgical procedures and with numerous surgical instruments. By way of non-limiting example, the methods and devices can be used in open surgical procedures. A person skilled in the art will also appreciate that while the methods and devices are described in connection with chondral cartilage repair, the methods and devices can be used in other tissue repairs related to the knee, e.g., cartilage at the patella, or to other articulating surfaces, e.g., shoulder, ankle, hip, and elbow, and in any other type of tissue repair using a tissue replacement implant.

In an exemplary embodiment, a patient having a cartilage lesion at a defect site at the articular surface of a bone joint, such as the femoral condyle at the knee, can be prepared for tissue repair surgery. Through an arthrotomy incision, the knee joint can be opened and the defect site exposed. The size and shape of the lesion can vary, although a lesion at the femoral condyle traditionally has an elliptical shape having a surface area of about 10 cm$^2$ (1000 mm$^2$). The undesirable cartilage tissue, which can include fibrillations and fissures, can be removed, to form a cavity in the tissue. An amount of healthy cartilage adjacent the lesion can also be removed in the process of removing the lesion. Debridement of the articular surface can be deep enough to expose a calcified layer of cartilage and/or a subchondral bone surface, e.g., in a range of about 2 to 3 mm below a top surface of the cartilage, for receiving a tissue repair implant. The bone surface can provide a substantially smooth surface for placement of the implant and a stable structure to which the implant can be attached. Once the articular surface has been properly prepared, the tissue repair implant can be implanted into the cavity formed in the cartilage and onto the articular surface. In some embodiments, a portion of the bone can be removed, and the implant can be implanted into the cavity formed in the cartilage and in the bone.

Before the implant is placed into a patient, the implant can be created using viable tissue, e.g., living, non-destroyed tissue cells, harvested from the patient in a first surgical procedure separate from a surgical procedure in which the implant is delivered to the patient, such as in autologous chondrocyte implantation (ACI) procedure, e.g., a procedure using a MACI® implant (available from Genzyme Corporation of Cambridge, Mass.). Although, a person skilled in the art will appreciate that the viable tissue can also or instead be gathered during the same surgical procedure in which the implant is attached to the patient.

Viable tissue can be collected from the patient in any way, as will be appreciated by a person skilled in the art. Various non-limiting embodiments of methods and devices for collecting tissue from a patient, such as in a biopsy procedure, can be found in U.S. Pat. No. 7,115,100 issued Oct. 3, 2006 entitled "Tissue Biopsy And Processing Device," U.S. Patent Publication No. 2008/0234715 filed Mar. 27, 2008 entitled "Tissue Extraction and Collection Device," and U.S. Patent Publication No. 2005/0059905 filed Sep. 11, 2003 entitled "Tissue Extraction and Maceration Device," which are hereby incorporated by reference in their entireties.

The source of viable tissue can vary, and the tissue can have a variety of configurations, but in an exemplary embodiment the harvested tissue includes chondrocytes. In an exemplary embodiment, once a sample of viable tissue has been obtained, the tissue sample can be processed under sterile conditions to create a suspension having at least one minced, or finely divided tissue particle. It is also possible to harvest the tissue in minced form such that further processing is not necessary. A person skilled in the art will appreciate that minced viable tissue fragments are simply small portions of living, non-destroyed tissue and that minced tissue fragments can enhance the effectiveness of the regrowth and healing response. The particle size of each tissue fragment can vary. By way of non-limiting example, the tissue size can be in the range of about 0.001 to 3 mm$^3$, but preferably the tissue particle is less than about 1 mm$^3$. In another embodiment, the viable tissue can be in the form of a tissue slice or strip harvested from healthy tissue that contains viable cells capable of tissue regeneration and/or remodeling, as described in U.S. Patent Publication No. 2005/0125077 filed Dec. 5, 2003 and entitled "Viable Tissue Repair Implants and Methods of Use," which is hereby incorporated by reference in its entirety. The tissue slice can be harvested to have a geometry that is suitable for implantation at the site of the injury or defect, and the harvested tissue slice can be dimensioned to allow the viable cells contained within the tissue slice to migrate out and proliferate and integrate with tissue surrounding the repair site. A person skilled in the art will appreciate that tissue can be collected from the patient and/or a compatible donor, that the tissue can be artificial tissue material, and that any combination of harvested tissue and artificial tissue material can be used.

Viable tissue harvested from a patient can optionally be combined with a variety of other materials, including carriers, such as a gel-like carrier or an adhesive. The viable tissue can also be contacted with a matrix-digesting enzyme to facilitate tissue migration out of the extracellular matrix surrounding the viable tissue. The enzymes can be used to increase the rate of cell migration out of the extracellular matrix and into the implant. Various non-limiting embodiments of gel-like carriers, adhesives, and enzymes can be found in U.S. Patent Publication No. 2005/0177249 filed Feb. 9, 2004 entitled "Scaffolds With Viable Tissue," which is hereby incorporated by reference in its entirety. Other non-limiting embodiments of viable tissue sources and methods for preparing viable tissues are disclosed in U.S. Patent Publication No. 2005/0113937 filed on Nov. 26, 2003 entitled "Conformable Tissue Repair Implant Capable Of Injection Delivery," which is hereby incorporated by reference in its entirety.

The viable tissue and any material combined with the viable tissue can be loaded onto a tissue scaffold. The scaffold can have a variety of configurations, as will be appreciated by a person skilled in the art. Generally, the scaffold can be formed using virtually any material or delivery vehicle that is biocompatible, bioimplantable, easily sterilized, and that has sufficient structural integrity and/or physical and mechanical properties to effectively provide for ease of handling in an operating room environment and to permit it to accept and retain one or more securing mechanisms, e.g., sutures, staples, adhesive, etc., without substantially tearing. By way of non-limiting example, the scaffold can be in the form of a matrix that is formed from a variety of any one or more materials, including resorbable materials, non-biological materials, and/or synthetic materials. The scaffold can be flexible so as to allow the scaffold to conform to the shape and dimensions of the target site of implantation. The scaffold can also include a bioabsorbable and/or bioresorbable component to act as a temporary carrier to improve handling of the implant during transportation. Various non-limiting embodiments of tissue scaffolds can be found in previously mentioned U.S. Patent Publication No. 2005/0177249 filed Feb. 9, 2004 entitled "Scaffolds With Viable Tissue," and in U.S. Patent Publication No. 2004/0078090 filed Feb. 25, 2003 entitled "Biocompatible Scaffolds With Tissue Fragments," U.S. Patent Publication No. 2005/0038520 filed Aug. 11, 2003 entitled "Method And Apparatus For Resurfacing An Articular Surface," and U.S. Pat. No. 6,884,428 issued Apr. 26, 2005 entitled "Use of Reinforced Foam Implants with Enhanced Integrity For Soft Tissue Repair And Regeneration," which are hereby incorporated by reference in their entireties.

Tissue harvested from a patient can be prepared and applied to a scaffold in any way, as will be appreciated by a person skilled in the art. The tissue component can be added to the scaffold during or after manufacture of the scaffold or before or after the implant is installed in a patient. Optionally, a bioactive agent can be incorporated within and/or applied to the tissue scaffold, and/or it can be applied to the viable tissue. Preferably, the bioactive agent is incorporated within, or coated on, the scaffold prior to the addition of viable tissue to the scaffold. The bioactive agent(s) can be selected from among a variety of effectors and cells that, when present at the site of injury, promote healing and/or growth or regeneration of the affected tissue. Various non-limiting embodiments of effectors and cells can be found in previously mentioned U.S. Patent Publication No. 2005/0177249 filed Feb. 9, 2004 entitled "Scaffolds With Viable Tissue." Various non-limiting embodiments of applying tissue, e.g., minced viable tissue, to a scaffold can be found in U.S. Patent Publication No. 2004/0193071 filed Mar. 28, 2003 entitled "Tissue Collection Devices And Methods," which is hereby incorporated by reference in its entirety.

As mentioned above, once a tissue scaffold is available for implantation into a patient, the patient can be prepared for the scaffold's implantation by removing cartilage to create a hole or cavity in the cartilage that extends from a surface of the cartilage to the underlying femoral condyle, or other site, as mentioned above. The defect site can be prepared for scaffold implantation in a variety of ways. In an exemplary embodiment, a surgical scribing tool configured to mark a predetermined shape in tissue can be arthroscopically used to form a cut having a predetermined shape in the cartilage such that the marked shape encloses the lesion, as discussed further below. Cartilage can be removed from within the marked shape such that the marked shape can define a perimeter of the tissue cavity in which the scaffold can be implanted. In some embodiments, also discussed further below, the scribing tool can be used to mark multiple shapes in the cartilage, each of the shapes overlapping at least a portion of the lesion and optionally overlapping at least one additional marked shape. The shapes can also be altered and/or connected using the same and/or additional scribing tools. The cartilage within the combined marked shape can be removed to define the shape of the scaffold-receiving cavity.

FIGS. 1-5 illustrate one exemplary embodiment of a compass-style surgical scribing tool 10 configured to mark, e.g., slice, score, etc., a predetermined circular shape in tissue. The scribing tool 10 can also be configured to cut tissue. The scribing tool 10 includes an outer shaft 12 and an inner shaft 14 configured to be movable relative to one another. Generally, the outer shaft 12 can be configured to rotate clockwise and/or counterclockwise around the inner shaft 14 when the outer shaft 12 is disposed in an inner passageway 16 of the outer shaft 12 such that a distal scribing tip 18 of the outer shaft 12 can move in a circle and mark a circular shape when positioned against tissue.

The outer shaft 12 can have a variety of shapes and configurations. As shown in this embodiment, the outer shaft 12 includes an elongate body 20 having a handle 22 at a proximal end 12a of the outer shaft 12 and an angled arm 24 offset from the elongate body 20 at a distal end 12b of the outer shaft 12. The elongate body 20 can be substantially cylindrical-shaped, as shown, although the elongate body 20 can have any shape. The elongate body 20 can also have any size such that its longitudinal length can allow at least a portion of the outer shaft 12 to be inserted into a body cavity of a patient with at least the handle 22 being located outside the patient. The inner passageway 16 can extend longitudinally through the elongate body 20 and can have any size and shape, e.g., cylindrically-shaped, configured to allow the inner shaft 14 to be slidably disposed therein and for the outer shaft 12 to rotate around the inner shaft 14 when the inner shaft 14 is disposed in the passageway 16.

The handle 22 is illustrated as being located at a proximal-most end of the outer shaft 12, but the handle 22 can be located anywhere at the outer shaft's proximal end 12a. The handle 22 can be, for non-limiting example, a substantially cylindrical disc or knob as shown, although as will be appreciated by a person skilled in the art the handle 22 can have any size, shape, and configuration that allows the outer shaft 12 to be held outside the body. The illustrated disc or knob shape of the handle 22 can allow the handle 22 to be manipulated using one hand, which can free the other hand for other surgical tasks. The handle 22 can be held and manipulated to help insert the outer shaft 12 into a patient, rotate the outer shaft 12 within the patient, and remove the outer shaft 12 from the patient. The passageway 16 can extend through the handle 22 to allow the inner shaft 14 to be slidably disposed therein. A diameter D1 of the passageway 16 can therefore be smaller than a diameter D2 of the handle 22. In some embodiments, such as if the handle is configured as a grippable handhold extending at a non-zero angle from one or more discrete locations around a perimeter of the elongate body 20, the passageway 16 can be separate from the handle 22. The diameter D2 of the handle 22 can also be larger than a diameter D3 of the elongate body 20, which can help the handle 22 serve as a stop mechanism configured to prevent the outer shaft 12 from being fully distally advanced into a body of a patient through an opening used to insert a distal portion of the outer shaft 12 into the patient's body. The passageway 16, the handle 22, and the elongate body 20 can share a central longitudinal axis A, which can help the outer shaft 12 rotate around the central longitudinal axis A when the handle 22 is moved to rotate the outer shaft 12, as discussed further below. A person skilled in the art will appreciate that while the handle 22 can make the outer shaft 12 easier to manipulate, the outer shaft 12 need not include the handle 22 but instead be manipulated using, e.g., a proximal end of the elongate body 20.

The angled arm 24 can distally extend from the elongate body 20 at any angle α. The angle α can be non-zero and less than about 90°, e.g., in a range of about 20° to 70°, to allow the distal scribing tip 18 at a distal end of the arm 24 to form a distal-most end of the outer shaft 12. The distal scribing tip 18 can thus contact a tissue positioned distal to the outer shaft 12 without any other portion of the outer shaft 12 also contacting the tissue.

The arm 24 can have any longitudinal length with the distal scribing tip 18 radially extending a distance r from the central longitudinal axis A. The distance r thus can correspond to a radius of a circle formed by the distal scribing tip 18 when the outer shaft 12 is rotated around the central longitudinal axis A such that a center of the circle can be axially aligned with the central longitudinal axis A. In an exemplary embodiment, the distance r can be in a range of about 2.5 to 20 mm (about 5 to 40 mm diameter), e.g., about 5 to 10 mm (about 10 to 20 mm diameter).

Although the arm 24 is shown integrally formed with the elongate body 20, in some embodiments, the arm 24 can be a modular element configured to be removably coupled to the elongate body 20 in any way appreciated by a person skilled in the art, e.g., threadably attached, snap fit, etc. Modular arms can optionally be supplied with an outer shaft of a scribing tool as part of a kit, which can also include an inner shaft. In this way, arms of different sizes, e.g., having different radial distances r, can be coupled to the elongate body 20 to allow the outer shaft 12 to mark circles of different diameters during the same or different surgical procedures. The distance r can be varied by changing a longitudinal length of the arm 24 and/or the angle α between the arm 24 and the elongate body 20. The distance r can also be changed by manipulating the arm's longitudinal length, e.g. pushing out the arm 24 or changing the angle α, without replacing the arm 24, such as with a retractable arm having umbrella-type folds. In another embodiment, the cam mechanism can be in the form of a rigid wire guided to enter and exit the elongate body 20 at predetermined angles that are not necessarily the same. For non-limiting example, the wire can enter the elongate body 20 parallel to the central axis A. By controlling the feed of the wire into the elongate body 20, the distance r can be manipulated. A cam mechanism (not shown) can optionally be included with the arm to vary the distance r, which can allow non-circular, e.g., ovular, marks to be made using the arm.

The distal scribing tip 18 can have a variety of sizes, shapes, and configurations. The distal scribing tip 18 can generally include a scribing edge, e.g., a knife blade, a needle, a water jet, a bovie, a harmonic scalpel, etc., configured to mark tissue. The distal scribing tip 18 can have a non-circular scribing edge such that the scribing tip 18 can be used as a stylus configured to "draw" a line, such as a line forming a circumference of a circle. The distal scribing tip 18 can be configured to be sharp enough to cut through tissue but not sharp enough to significantly cut bone underlying tissue to help minimize damage to the bone. The distal scribing tip 18 can be configured to mark a line having any width w, such as a thin line having a width of a traditional knife edge, e.g., about 0.2 mm, or a thicker line or trough having a larger width, e.g., about 3 mm. A larger scribing tip width w can allow the outer shaft 12 to mark more cartilage and thereby reduce an amount of cartilage to be cleared from within the shape defined by a line marked by the distal scribing tip 18.

The inner shaft 14 can also have a variety of configurations. As shown in this embodiment, the inner shaft 14 includes an elongate body 26 having a handle 28 at a proximal end 14a of the inner shaft 14 and at least one cartilage-engaging element 30 at a distal end 14b of the inner shaft 14. The inner shaft 14 can have any longitudinal length, but in an exemplary embodiment the inner shaft 14 can be longer than the outer shaft 12 to allow the inner shaft 14 to be disposed in the passageway 16 and simultaneously distally extend beyond the outer shaft's distal end 12b and proximally extend beyond the outer shaft's proximal end 12a. The handle 28 can be similar to the outer shaft's handle 22, although the handles 22, 28 can be different from each other and need not be the same as shown in the scribing tool 10.

As mentioned above, the inner shaft 14 can be configured to be removably coupled to the outer shaft 12 with the inner shaft's elongate body 26 slidably received within the inner passageway 16 of the outer shaft 12. The inner shaft's elongate body 26 can thus, as shown in this embodiment, be substantially cylindrical-shaped to match the shape of the inner passageway 16. The outer shaft's passageway 16 and the inner shaft's elongate body 26 having corresponding cylindrical shapes can allow the inner shaft 14 to be both linearly and rotatably movable within the inner passageway 16. The inner shaft's elongate body 26 can thus have a diameter D4 less than the diameter D1 of the outer shaft's inner passageway 16 to allow the elongate body 26 to be movable therein. Conversely, the inner shaft's handle 28 can have a diameter D5 that is greater than the diameter D1 of the outer shaft's passageway 16 and greater than the elongate body's diameter D4. In this way, the inner shaft's handle 28 can serve as a stop mechanism, similar to the stop mechanism discussed above, configured to limit a distance that the distal end 14b of the inner shaft 14 extends beyond the distal end 12b of the outer shaft 12.

Although the inner shaft 14 can be a solid member as shown, the inner shaft 14 can include one or more passageways formed therethrough. For non-limiting example, the inner shaft 14 can include a tunnel extending through its distal and proximal ends 14b, 14a that is configured to receive at least one surgical instrument disposed therethrough, e.g., a vacuum device configured to suction fluid, tissue, etc. away from a surgical site.

The one or more cartilage-engaging elements 30 at the inner shaft's distal end 14b can generally be configured to help secure the inner shaft 14 against cartilage and/or bone when the inner shaft 14 is disposed through the outer shaft 12. In an exemplary embodiment, the cartilage-engaging elements 30 can be configured to contact cartilage without penetrating into bone to help avoid inflicting any damage to the bone. In some embodiments, the cartilage-engaging elements 30 can be configured to not contact bone at all but only contact cartilage or other tissue to help stabilize the inner shaft 14. The cartilage-engaging elements 30 can have any size, shape, and configuration. Although two cartilage-engaging elements 30 are shown, the inner shaft 14 can include any number of cartilage-engaging elements 30. Moreover, each of the cartilage-engaging elements 30 can be the same or different from any other of the cartilage-engaging elements 30. The cartilage-engaging elements 30 can be configured as spikes or prongs as shown, with or without tapered distal tips configured to help the cartilage-engaging elements 30 penetrate bone. The cartilage-engaging elements 30 can be arranged at the inner shaft's distal end 14b in any configuration, such as equidistantly spaced radially around a central longitudinal axis A2 of the inner shaft 14, as illustrated. In an embodiment where the inner shaft has a single cartilage-engaging element, the single cartilage-engaging element can be substantially axially aligned with the central longitudinal axis A2. In some embodiments including a plurality of the cartilage-engaging elements 30, the cartilage-engaging elements 30 can cover a distal end surface of the elongate body 20 such that the cartilage-engaging elements 30, e.g., a plurality of teeth, can form a textured cartilage-engaging surface configured to grip cartilage and/or bone without penetrating into the cartilage and/or bone.

Although the cartilage-engaging elements 30 are shown integrally formed with the elongate body 26, any one or more of the cartilage-engaging elements 30 can be movably coupled to the elongate body 26. For non-limiting example, the cartilage-engaging elements 30 can be retractable such that in an extended position the cartilage-engaging elements 30 can extend distally beyond the inner shaft's distal end 14b and in a retracted position can be contained within the elongate body 26. Retraction and extension of movable cartilage-engaging elements can be controlled in any way, as will be appreciate by a person skilled in the art, such as through actuation of a control mechanism, e.g., a knob, a button, a lever, an electronic signal communicator, etc., at the proximal end 14a of the inner shaft 14.

Figure 6:
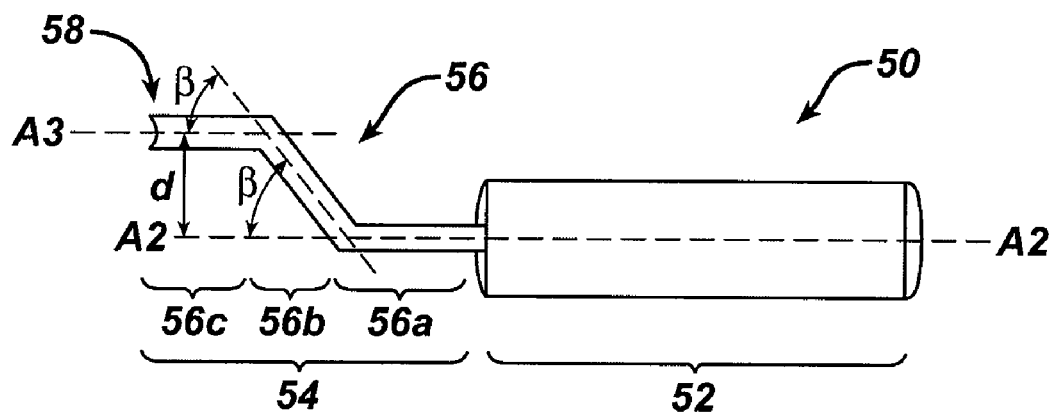
FIG. 6 is a side view of one embodiment of a scribing tool having a curved distal scribing tip.

FIG. 6 illustrates another embodiment of a scribing tool. In this embodiment, the tool is a wood cutter-style surgical scribing tool 50 configured to mark a circular shape in tissue. The scribing tool 50 can include a proximal handle portion 52 and a distal shaft portion 54. The handle portion 52 can include any type of handle as will be appreciated by a person skilled in the art, such as a cylindrical hand grip as shown. The handle portion 52 can optionally include one or more gripping mechanisms, e.g., finger loops, molded finger depressions, treads, etc., to help a hand hold and rotate the scribing tool 50. The shaft portion 54 can include a shaft 56 extending distally from the handle portion 52 and having a distal scribing tip 58 at a distal end of the shaft 56. Generally, the scribing tool 50 can be rotated clockwise and/or counterclockwise around a longitudinal axis of the scribing tool 50, e.g., a central, proximal longitudinal axis A2, such that the distal scribing tip 58 can move in a circle around the longitudinal axis A2 and mark a circular shape when the distal scribing tip 58 is positioned against tissue.

The shaft 56 can have any configuration. The shaft 56 can include a rigid elongate member having a distal portion 56c that is radially offset from a proximal portion 56a with an angled mid-portion 56b located between the proximal and distal portions 56a, 56c. The shaft's distal portion 56c can be offset by any radial distance d and at any angle β from the proximal portion 56a. As shown in the illustrated embodiment, the mid-portion 56b can distally extend from the proximal portion 56a at the angle β, and the distal portion 56c can distally extend from the mid-portion 56b at the angle β such that the longitudinal axis A2 of the proximal portion 56a can be parallel to a longitudinal axis A3 of the distal portion 56c. In this way, the scribing tool 50 can be rotated with the distal scribing tip 58 most effectively positioned to mark the tissue. The shaft 56 can extend from a center of the handle portion 52 as illustrated such that the longitudinal axis A2 of the handle portion 52 axially aligns with the longitudinal axis of the proximal portion 56a of the shaft 56. In this way, a center of a circle marked by the distal scribing tip 58 can have its center substantially aligned with the longitudinal axis A2 of the scribing tool 50.

Although the shaft 56 is shown integrally formed with the handle portion 52, in some embodiments, the shaft 56 can be a modular element configured to be removably coupled to the handle portion 52 in any way appreciated by a person skilled in the art, e.g., threadably attached, snap fit, etc. In this way, shafts of different sizes, e.g., configured to mark circles having different radii, can be coupled to the handle portion 52. Modular shafts can optionally be supplied with a handle portion as part of a kit.

Although the shaft 56 can be a solid member as shown, the shaft 56 can include one or more passageways formed therethrough. For non-limiting example, the shaft 56 can include a tunnel extending through at least its proximal portion 56a that is in communication with a tunnel extending through the handle portion 52. The shaft and handle portion's tunnel can be configured to receive at least one surgical instrument disposed therethrough, e.g., a vacuum device configured to suction fluid, tissue, etc. away from a surgical site or a stabilizing tool such as the inner shaft 14, or a positioning tool configured to penetrate bone to aid the tool 50 in rotating about its axis A2.

The shaft 56 can also have any size and shape. As illustrated in this embodiment, the shaft 56, or at least the distal portion 56c thereof, can be in the form of a bar or rod having an arcuate, c-shaped cross-sectional shape. The distal scribing tip 58 can thus have an arcuate, c-shaped cross-sectional shape configured to allow the scribing tool 50 to mark a circle in tissue when the scribing tool 50 is rotated about the longitudinal axis A2 of the scribing tool 50. In some embodiments, the shaft 56 can have one or more other cross-sectional shapes in addition to or instead of a c-shape along its length, e.g., circular, square, triangular, etc., provided that a scribing edge of the distal scribing tip 58 has an arcuate shape.

The distal scribing tip 58 can have a variety of sizes, shapes, and configurations, similar to that discussed above regarding the distal scribing tip 18 of the scribing tool 10. The distal scribing tip 58 can have any radius of curvature configured to mark a line forming a circumference of a circle having a radius equal to the radius of curvature of the distal scribing tip 58. In an exemplary embodiment, the radius of curvature of the distal scribing tip 58 can be in a range of about 2.5 to 20 mm, e.g., about 5 mm. The curvature of the distal scribing tip 58 can help guide the distal scribing tip 58 in a circular motion when the scribing tool 50 is rotated about the central longitudinal axis A2, as discussed further below. The scribing tool 50 can optionally include a center pin (not shown) axially extending from the proximal portion 56a of the shaft and/or the handle 52 that is configured to penetrate cartilage and stabilize the tool 50 without preventing rotational motion of the tool 50 to allow a circular mark to be created using the distal scribing tip 18.

Figure 7:
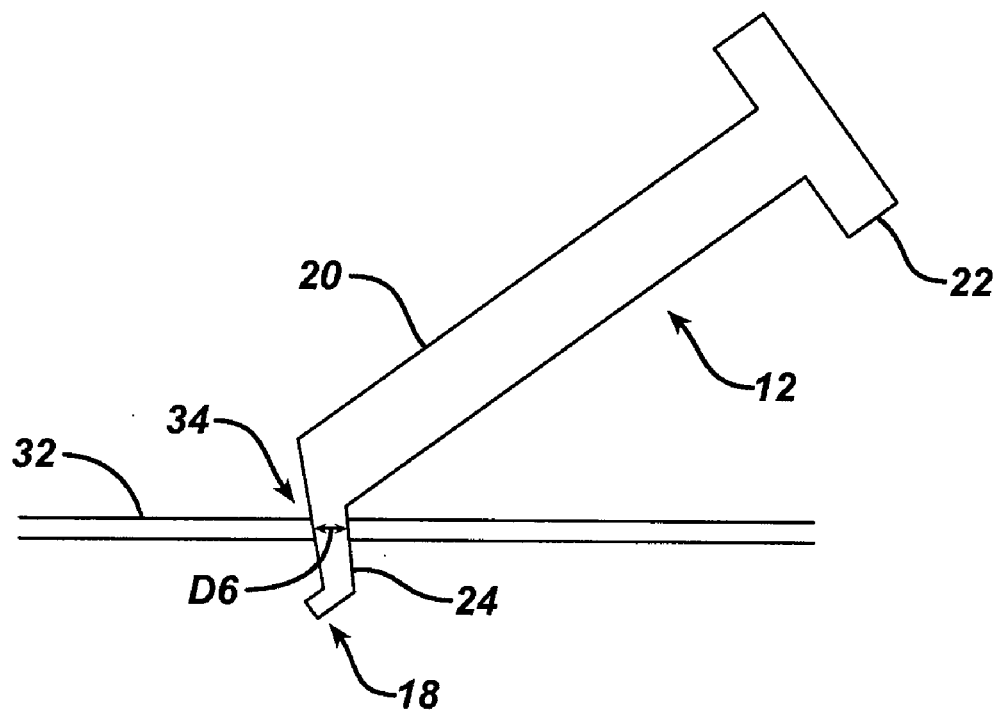
FIG. 7 is a partial cutaway view of the outer shaft of FIG. 1 being advanced through tissue of a patient.

Regardless of the scribing tool introduced into a body of a patient to mark at least one circle in tissue, the scribing tool can be introduced into the patient's body in any way, as will be appreciated by a person skilled in the art. In one embodiment illustrated in FIG. 7, a scribing tool, e.g., the scribing tool 10, can be inserted into a body cavity through a surgically created incision or opening 34 in a tissue 32. Although only the outer shaft 12 is shown being initially introduced through the tissue 32, a person skilled in the art will appreciate the inner shaft 14 can be introduced through the tissue 32 before, with, or preferably after, the outer shaft 12. A person skilled in the art will also appreciate that the scribing tool 10 can be inserted directly through the tissue 32 as illustrated, or the scribing tool 10 can be inserted through an introducer device, e.g., a surgical instrument such as a cannula, a trocar, an endoscope, etc. that has a working channel through which another surgical instrument can be advanced.

Introducing the outer shaft 12 into the patient before the inner shaft 14, or with the inner shaft 14 only partially advanced into the passageway 16, can allow the outer shaft's distal arm 24 to be inserted first through the tissue 32 at an angle such that the opening in tissue can have a size less than the diameter of the circular mark to be formed using the distal scribing tip 18. The distal scribing tip 18 can help form the opening 34 and/or one or other surgical tools can be used to form the opening 34, as will be appreciated by a person skilled in the art. Because the distal arm 24 can have a width that is smaller than its longitudinal length r, the diameter D3 of the outer shaft's elongate body 20, the diameter D1 of the outer shaft's passageway 16, and the diameter D4 of the inner shaft's elongate body 26, it can thus be inserted through an incision having a diameter D6 of about the arm's width. The arm 24 can optionally be used to widen the opening 34 as the outer shaft 12 is advanced therethrough. The outer shaft's elongate body 20 can expand the diameter of the opening 34 to about the diameter D3 of the outer shaft's elongate body 20 as the elongate body 20 is passed therethrough, thereby helping to minimize the size of the opening 34 and to reduce patient trauma.

The outer shaft 12 can be longitudinally advanced any distance through the tissue 32 and positioned in any way relative to the tissue 32. The outer shaft 12 can also be positioned in any way relative to the tissue defect site desired to be mark using the scribing tool 10. In an exemplary embodiment, the outer shaft 12 can be positioned through the tissue 32 such that its longitudinal axis A is substantially perpendicular to the defect site. Such substantially perpendicular positioning can help more accurately position the arm 24 from outside the patient's body with respect to tissue and move the arm 24 more quickly and easily to mark the target tissue.

Once the outer shaft 12 has been passed through the tissue 32 with, e.g., the elongate body 20 positioned within the opening 34 with the handle 22 and the arm 24 on opposed sides of the tissue 32, the inner shaft 14 can be advanced into the passageway 16 through the outer shaft's proximal end 12a. The central longitudinal axes A, A2 of the outer and inner shafts 12, 14, respectively, can be substantially aligned and positioned at a desired location relative to the tissue defect site. The inner shaft's cartilage-engaging elements 30 can extend through tissue at the defect site and engage bone to provide friction to help mount the scribing tool 10 in a stable position for scribing tissue using the distal scribing tip 18. Bone surfaces can be non-planar, so if the cartilage-engaging elements 30 are configured with sharp tips to penetrate into bone, the cartilage-engaging elements 30 can be penetrated into bone at varying depths, and/or one or more of the cartilage-engaging elements 30 may not penetrate bone at all.

Figure 8A:
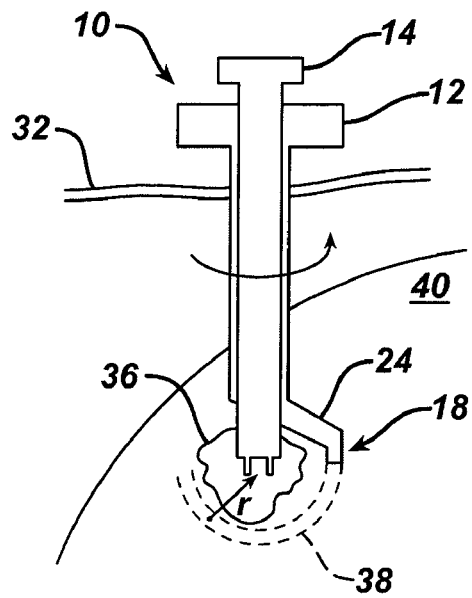
FIG. 8A is a partial cutaway view of the inner shaft of FIG. 4 disposed in the outer shaft of FIG. 7, and the outer shaft being rotated around the inner shaft to mark a line in tissue that at least partially surrounds a tissue defect site.

With the scribing tool 10 advanced through the tissue 32 and the inner shaft 14 engaging bone as desired, as illustrated in one embodiment in FIG. 8A, the outer shaft 12 can be rotated around the inner shaft 14, relative to the inner shaft 14 and a defect site 36 in cartilage 40, to rotate the arm 24 around the longitudinal axes A, A2 of the outer and inner shafts 12, 14, respectively. The outer shaft 12 can be manually rotated, e.g., with a hand holding the handle 22, and/or electronically rotated, such as in robotic surgery. The inner shaft 14 can be pressed down against bone underlying the defect site 36 during rotation of the outer shaft 12 to help stabilize the scribing tool 10. The rotation of the arm 24 can mark a line 38 in the cartilage 40 using the distal scribing tip 18. The arm 24 can be rotated about 360° so that the marked line 38 can form a closed path that defines a circumference of a circle having a radius r equal to the arm's length r. The marked circle can thus have a diameter greater than the diameter D6 of the opening 34 through which the scribing tool 10 was introduced into the patient. A person skilled in the art will appreciate that the arm 24 can be continuously rotated about 360° in one direction, e.g., counterclockwise as shown, or rotated any number of degrees clockwise and/or counterclockwise to mark a circle in the cartilage 40. As mentioned above, the line 38 can be scored any depth through the cartilage 40 toward bone underlying the cartilage 40. In an exemplary embodiment, the distal scribing tip 18 can be distally pushed until it is felt to contact bone to help the distal scribing tip 18 cut through the cartilage 40 down to bone to help ease removal of the cartilage 40 within the shape defined by the line 38. Because the outer shaft 12 can slide linearly relative to the inner shaft 14 in addition to moving rotationally around the inner shaft 14, the outer shaft 12 can slide up and down during its rotation around its central longitudinal axis A. Such slidable linear motion can allow the outer shaft 12 to compensate for a non-planar surface of the cartilage 40 and/or the bone underlying the cartilage 40 and continuously score the line 38 in the cartilage 40.

Figure 8B:
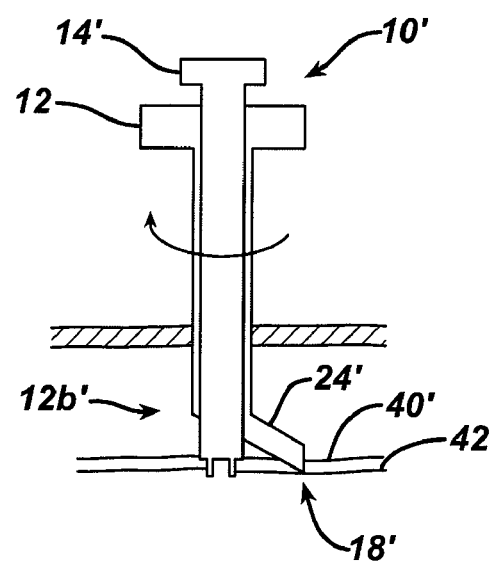
FIG. 8B is a partial cutaway view of the inner shaft of FIG. 4 disposed in another embodiment of an outer shaft of a scribing tool having a distal scribing arm, and the outer shaft being rotated around the inner shaft to mark a line in tissue that at least partially surrounds a tissue defect site.

FIG. 8B illustrates an alternate embodiment of a compass-style scribing tool 10' scribing cartilage 40' through to a bone surface 42. The scribing tool 10' includes an outer shaft 12' configured to slidably receive an inner shaft 14' therethrough, similar to the outer and inner shafts 12, 14 of scribing tool 10. The outer shaft 12' in this alternate embodiment, however, has a linear arm 24' at its distal end 12b'. The linear arm 24' does not include a bend at its distal end as in the arm 24 of the scribing tool 10 but instead has a pointed distal scribing tip 18'. The pointed distal scribing tip 18' can be configured to mark a thin line in the cartilage 40'.

Figure 9:
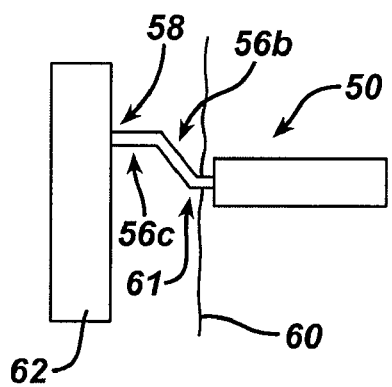
FIG. 9 is a partial cutaway view of the scribing tool of FIG. 6 advanced through tissue of a patient with the distal scribing tip positioned adjacent a tissue defect site.

As mentioned above, the wood cutter-style scribing tool 50 can be introduced into a body of a patient in any way and can be used to mark a circle in tissue in a way similar to the compass-style scribing tool 10. FIG. 9 illustrates one embodiment of the scribing tool 50 in an initial position extending through a surface tissue 60 and having its distal scribing tip 58 positioned adjacent tissue, e.g., cartilage 62, to be marked using the scribing tool 50. In an exemplary embodiment, the scribing tool 50 can be positioned through the tissue 60 such that the scribing tool's longitudinal axis A2 and the shaft's distal longitudinal axis A3 are substantially perpendicular to the defect site. The handle portion 52 can be positioned on an opposite side of the surface tissue 60 than at least a portion of the shaft 56, e.g., the distal portion 56c and the mid-portion 56b, which can help minimize a size of an opening 61 in the tissue 60 through which the scribing tool 50 is inserted since the handle portion 52 can be larger than the shaft portion 54.

Figure 10:
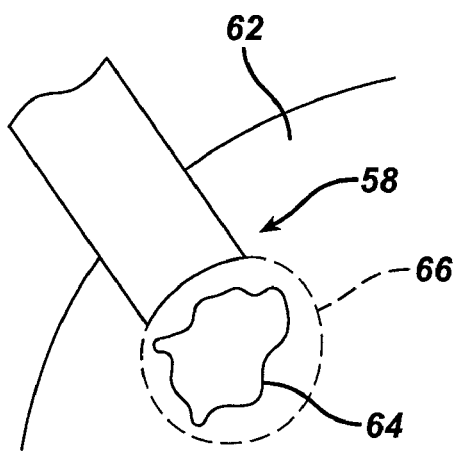
FIG. 10 is a partial perspective view of the scribing tool of FIG. 9 being rotated to mark a line in tissue that surrounds a tissue defect site.
Figure 11:
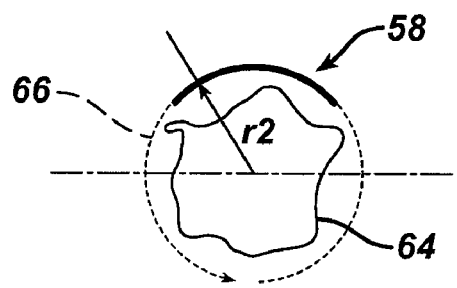
FIG. 11 is a top view of the scribing tool of FIG. 9 being rotated to mark a line in tissue that surrounds a tissue defect site.

With the scribing tool 50 advanced through the tissue surface 60 and the distal scribing tip 58 positioned adjacent the cartilage 62, the scribing tool 50 can be rotated to mark a circular line in the cartilage 62. The scribing tool 50 can be rotated generally similar to the rotation described above regarding the scribing tool 10. As illustrated in one embodiment in FIGS. 10 and 11, the scribing tool 50 can be rotated about 360° around the central longitudinal axis A2, relative to the cartilage 62, to mark a line with the distal scribing tip 58 that forms a circular shape 66 around a defect site 64 in the cartilage 62. The circular shape 66 has a radius r2 equal to the radius of curvature of the distal scribing tip 58.

Figure 12:
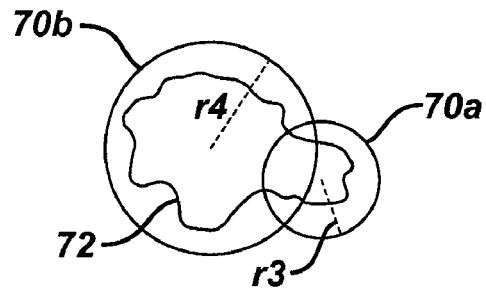
FIG. 12 is a top view of one embodiment of a first circular mark in tissue that partially surrounds a tissue defect site, and a second circular mark in tissue that overlaps a portion of the first circular mark and that partially surrounds the tissue defect site.

In some instances, a defect site can have a diameter larger than a diameter of a circle that the scribing tool used to mark a circle around the defect site can mark, or it can have an oblong shape making it undesirable to mark a single circle around since too much healthy tissue will be removed. Thus, as mentioned above, in some embodiments, a scribing tool such as any of the scribing tools 10, 10', 50, can be used to mark two or more circular shapes in tissue at a defect site to define a shape having a non-circular perimeter. If it is known that a plurality of circles that each partially overlap the defect site will be marked in tissue, a person skilled in the art will appreciate that any one or more of the circles can be partially marked in tissue, e.g., marked as c-shaped lines, such that the marked lines can form the non-circular perimeter shape in a similar way that the lines would form the non-circular perimeter shape were they marked as circular-shaped lines. The same scribing tool can be used to mark each of the circles to help minimize introduction and removal of surgical instruments into and out of the patient during the surgical procedure, although different scribing tools can be used. As shown in one embodiment of a mosaicplasty approach in FIG. 12, a plurality of marked circles, e.g., first and second circles 70a, 70b, can be marked in tissue to surround a tissue defect site 72 with each of the marked circles 70a, 70b partially overlapping at least one other marked circle 70a, 70b. Although two marked circles 70a, 70b are illustrated, a person skilled in the art will appreciate that any number of overlapping circles can be marked in tissue to ensure that the defect site 72 is enclosed by the marked circles 70a, 70b. A person skilled in the art will also appreciate that while the marked circles 70a, 70b are shown with the first circle 70a having a first radius r3 that is smaller than a second radius r4 of the second circle 70b, any of the plurality of marked circles can have a radius that is the same or different as any one or more of the other marked circles. The overlapping circles 70a, 70b can be marked in any order with respect to one another.

Figure 13:
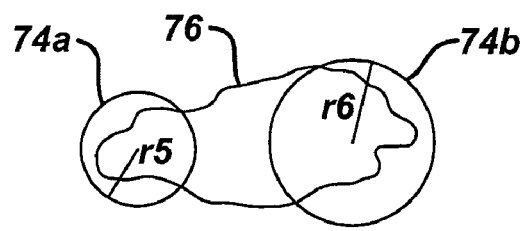
FIG. 13 is a top view of one embodiment of first and second circular marks in tissue that each partially surround a tissue defect site.
Figure 14:
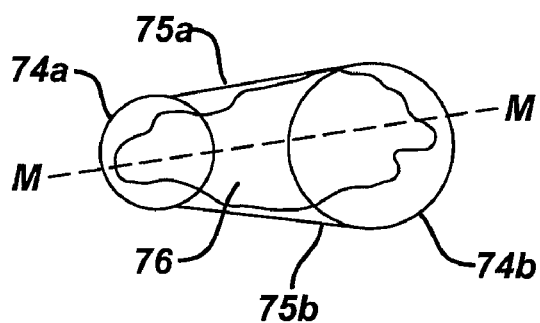
FIG. 14 is a top view of one embodiment of connecting lines marked in tissue to connect outer edges of the first and second circular marks of FIG. 13.
Figure 15:
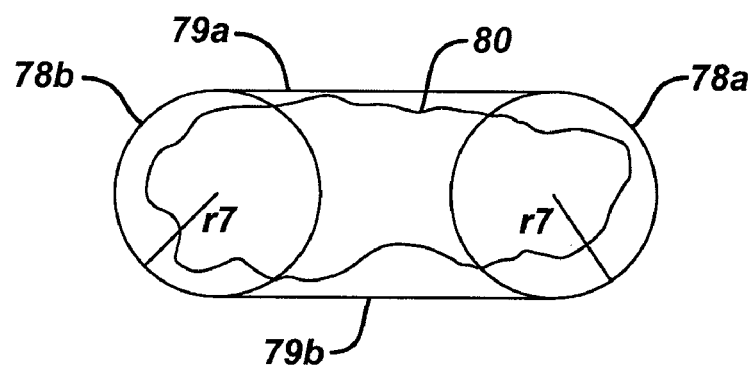
FIG. 15 is a top view of one embodiment of first and second circular marks in tissue to each partially surround a tissue defect site, and connecting lines marked in tissue that connect outer edges of the first and second circular marks.

In some embodiments, multiple circles can be marked in tissue to overlap opposed ends of a tissue defect site. Such an approach can be effective to help mark an ovular or oblong shape in tissue, which can be particularly useful in repairing a chondral defect since chondral defect sites can often have a generally ovular or oblong shape. FIGS. 13 and 14 illustrate an exemplary embodiment of an ovular-mark approach. First and second circles 74a, 74b can be marked in tissue to partially overlap a generally ovular or oblong-shaped tissue defect site 76 at opposed ends of the defect site 76, as illustrated in FIG. 13. The first and second circles 74a, 74b can be marked in any order with respect to one another. A person skilled in the art will appreciate that while the marked circles 74a, 74b are shown with the first circle 74a having a first radius r5 that is smaller than a second radius r6 of the second circle 74b, the first and second circles 74a, 74b can have a radius that is the same or different from one another. For non-limiting example, FIG. 15 illustrates an exemplary embodiment of first and second non-overlapping circles 78a, 78b having a same radius r7 marked at opposed ends of an ovular tissue defect site 80. A person skilled in the art will also appreciate that while the first and second circles 74a, 74b of FIGS. 13 and 14 are not overlapping as shown in this embodiment, marked circles at opposed ends of a tissue defect site can partially overlap each other.

With circles marked to overlap opposed ends of a tissue defect site, lines can be marked in the tissue around the defect site to connect the two circles. With the first and second circles 74a, 74b marked at opposed ends of the defect site 76, first and second connecting lines 75a, 75b can be marked in the tissue to connect the first and second circles 74a, 74b. The first and second circles 74a, 74b and first and second lines 75a, 75b can together define a perimeter of an ovular shape marked in the tissue that surrounds the defect site 76. The first and second lines 75a, 75b can be formed in tissue in any order and in any way using any surgical instrument configured to marked tissue with a scribing edge, as will be appreciated by a person skilled in the art. The first and second lines 75a, 75b can each be linear as illustrated with each of the lines 75a, 75b tangent to each of the first and second circles 74a, 74b, or one or both of the lines 75a, 75b can be non-linear and/or non-tangent. Similarly, referring to FIG. 15, first and second connecting lines 79a, 79b can be marked around the defect site 80 to connect the first and second circles 78a, 78b and form an oblong shape around the defect site 80.

Figure 16:
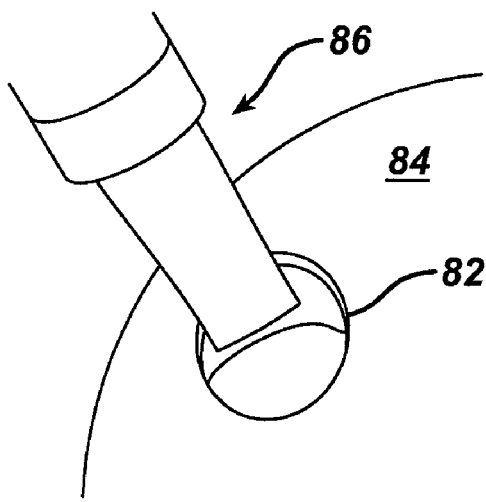
FIG. 16 is a partial perspective view of one embodiment of a scraper clearing tissue from within a shape marked in tissue to form a cavity.
Figure 17:
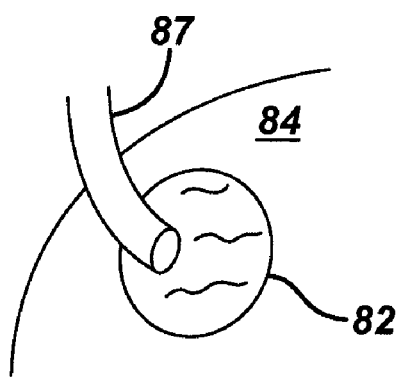
FIG. 17 is a partial perspective view of one embodiment of a suction device suctioning tissue from within the cavity cleared by the scraper of FIG. 16.
Figure 18:
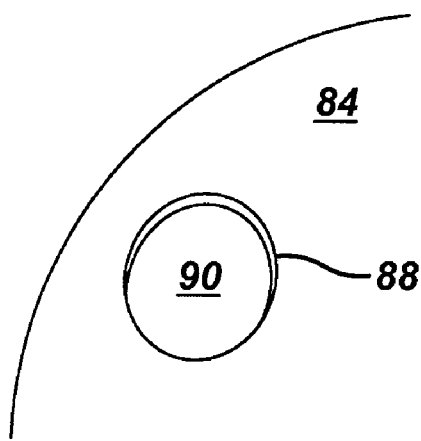
FIG. 18 is a partial perspective view of the cavity of FIG. 17 with tissue cleared and suctioned from within the cavity.

Once a desired one or more circles have been marked around a tissue defect site and, optionally, connecting lines are marked to connect marked circles, the tissue within the perimeter defined by the marked circle(s) and lines can be removed. Such removal can clear the defect from the tissue, potentially along with a minimal amount of healthy tissue adjacent the tissue defect site, to form a cavity in the tissue for receipt of a tissue replacement implant. The tissue within the shape's perimeter can be cleared in any way using any surgical tool, e.g., a curette, a scraper, the distal scribing tip 58 of the scribing tool 50, etc., as will be appreciated by a person skilled in the art, such as by creating a perpendicular edge between the tool and the tissue to be cleared. FIG. 16 illustrates one embodiment of tissue within a circular shape 82 marked in cartilage 84 being cleared using a flat-edged scraper 86. FIG. 17 shows excess cartilage scraped from within the circle 82 being suctioned away from the surgical site using a suction device 87, which can be any surgical device configured to vacuum or suction away tissue, as will be appreciated by a person skilled in the art. As shown in FIG. 18, a cavity 90 defined by the perimeter or circumference of the shape marked in the cartilage 84 can be formed in the cartilage 84 down to bone 90 underlying the cartilage 84 after tissue has been removed from within the shape.

With tissue cleared as desired from within the marked shape to form a cavity, a tissue replacement implant can be prepared for delivery to and fastening within the cavity. The implant is traditionally created larger than an expected size of the cavity, e.g., a size larger than the defect site, and cut during the surgical procedure down to a size and shape substantially matching the cavity. In this way, the implant can be cut from a portion of the prepared tissue replacement implant that includes a high concentration of deposited tissue, as tissue traditionally adheres in varying concentrations across a tissue replacement implant. Moreover, the size of the cavity formed during a surgical procedure can be greater or less than expected, e.g., if the defect site is larger than previously determined, if more healthy tissue is removed than originally intended, etc. Cutting the implant to size during the procedure can thus help match the implant's size to the cavity's actual size to form a close fit and fill the entire cavity.

Figure 19:
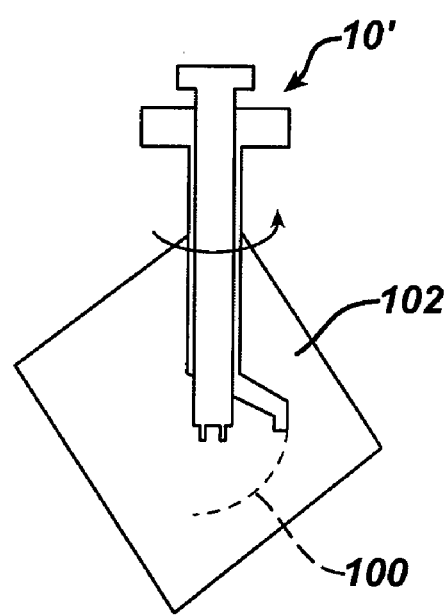
FIG. 19 is a partial cutaway perspective view of the inner and outer shafts of FIG. 8B being used to cut a tissue scaffold.
Figure 20:
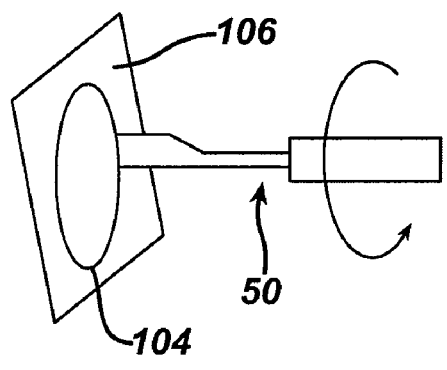
FIG. 20 is a perspective view of the scribing tool of FIG. 6 being used to cut a tissue scaffold.

The tissue replacement implant can be trimmed to a desired size in any number of ways. In an exemplary embodiment, a tissue replacement implant can be cut from a larger prepared implant using a scribing tool that was used to mark at least one circle in the tissue to receive the implant. In one embodiment shown in FIG. 19, the compass-style scribing tool 10' of FIG. 8B can be used to cut a line 100 in a prepared tissue replacement implant 102 to form a circular shape in a similar way to how the scribing tool 10' can mark a circular shape in tissue. In another embodiment shown in FIG. 20, the wood cutter-style scribing tool 50 of FIG. 6 can cut a line 104 in a prepared tissue replacement implant 106 to form a circular shape in a similar way to how the scribing tool 50 can mark a circular shape in tissue. Using the same scribing tool to mark the cavity's shape and to cut the implant can help substantially match the size of the cavity and the size of the implant. A person skilled in the art will appreciate that while the same individual scribing tool can be used to form the cavity's shape and the implant, a different but similarly configured scribing tool, such as a punch, can be used that is configured to cut a circle of the same predetermined diameter as the scribing tool used to cut the cavity's shape. Using a different but similarly configured scribing tool can be cleaner and faster than using the same scribing tool, although chances of size error can be reduced by using the same device on both the tissue and the implant.

Figure 21:
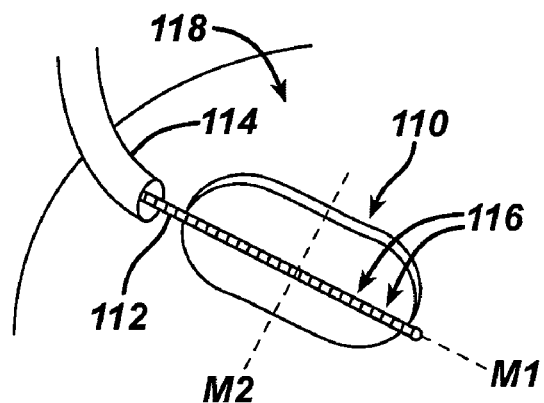
FIG. 21 is a partial perspective view of one embodiment of a measuring device measuring a size of a cavity formed in tissue.

In another exemplary embodiment, a template tool can be used to help cut a desirably sized tissue replacement implant. The template tool can have a variety of configurations and can be used in a variety of ways to size an implant. Prior to using the template tool to help cut the implant, a size of the cavity formed at the defect site in tissue can be measured. In one embodiment shown in FIG. 21, a cavity 110 cut in tissue 118 in any way can be measured using a measuring device 112 to determine a size of the cavity 110. The measuring device 112 can be configured to gauge a distance between at least two points in a body of a patient, e.g., an elongate shaft having markings 116 that are configured to be introduced into the patient through an introducer device 114. The cavity 110 can be measured in a first direction along a major axis M1 of the cavity 110 to determine a length of the cavity 110 and/or in a second direction along a minor axis M2 of the cavity 110 to determine a width of the cavity 110. The length of the cavity 110 along the minor axis M2 can, however, be predetermined prior to formation of the cavity 110, such as when opposed ends of the cavity 110 are formed using a scribing tool including a distal scribing tip configured to cut a circle having a predetermined radius, e.g., any of the scribing tools 10, 10', 50. Further, if the cavity 110 is circular, instead of ovular as shown in FIG. 21, a person skilled in the art will appreciate that the major and minor axes M1, M2 would be identical and their lengths determined with one diameter or radius measurement, unless such a measurement is not taken because the cavity's radius is known as a predetermined value. A person skilled in the art will also appreciate that measurements of the cavity 110 can be exact or approximate. By knowing a length and width of the cavity 110, or simply its diameter or radius, a tissue replacement implant can be cut to a size and shape to substantially match the size and shape of the cavity 110.

Figure 22:
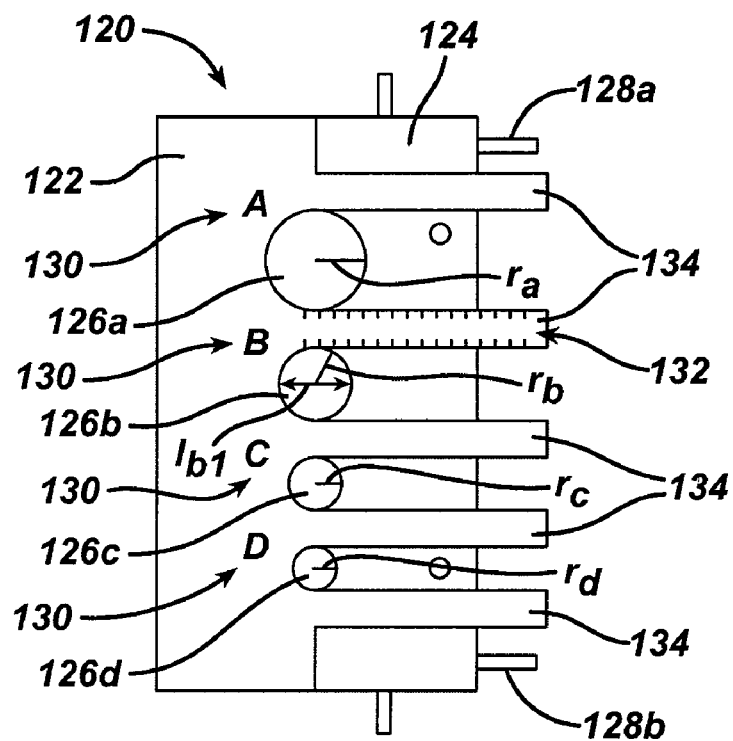
FIG. 22 is a top view of one embodiment of an adjustable template tool in an unexpanded position.

In an exemplary embodiment using a template tool to help size a tissue replacement implant, the template tool have an adjustable template tool with at least one adjustable opening. As shown in one embodiment in FIGS. 22 and 23, an adjustable template tool 120 can include first and second movable members 122, 124 configured to define a plurality of adjustable openings 126a, 126b, 126c, 126d. Although first, second, third, and fourth openings 126a, 126b, 126c, 126d are shown, the template tool 120 can include any number of adjustable openings. The first and second movable members 122, 124 can be configured to be movable relative to one another with both of the movable members 122, 124 being movable, although a person skilled in the art will appreciate that only one of the movable members 122, 124 can be configured to move while the other of the movable members 122, 124 remains stationary.

In this illustrated embodiment, the second movable member 124 can be linearly slidably movable relative to the first movable member 122. The second movable member 124 can be linearly slidably movable in any, such as by being slidable in a plane parallel to or co-planar with a plane of the first movable member 122 along connecting rods 128a, 128b coupling the first and second movable members 122, 124. The template tool 120 is shown in an unexpanded position in FIG. 22 where each of the openings 126a, 126b, 126c, 126d have a circular shape. Moving the first and second movable members 122, 124 relative to one another can move the template tool 120 from the unexpanded position to an expanded position shown in FIG. 23 where each of the openings 126a, 126b, 126c, 126d have an oblong shape. A person skilled in the art will appreciate that the openings 126a, 126b, 126c, 126d can be simultaneously adjusted in size as illustrated in this embodiment, or any one or more of the openings 126a, 126b, 126c, 126d can be adjusted individually or concurrently with any number of the other openings 126a, 126b, 126c, 126d.

The template tool 120 can be configured to size a variety of openings each having a different minor axis length, e.g., openings created using scribing tools having different predetermined radii. In the illustrated embodiment, each of the openings 126a, 126b, 126c, 126d can be circular shaped having a different respective radius $r_a$, $r_b$, $r_c$, $r_d$ when the template tool 120 is in the unexpanded position. By sliding the second movable member 124 any distance linearly away from the first movable member 122 to move the template tool 120 to an expanded position, the size of each of the openings 126a, 126b, 126c, 126d can be increased with a minor axis length of each of the openings 126a, 126b, 126c, 126d remaining constant, e.g., opposed ends of the oval shape having a predetermined radius of curvature, but with a major axis length of each of the openings 126a, 126b, 126c, 126d increasing. Thus, using the second opening 126b as a non-limiting example, a length $l_{b1}$ of the second opening 126b, equal to double the circular radius $r_b$, can be increased to an expanded length $l_{b2}$ as the second opening 126b changes shape from a circle in the unexpanded position to an oval in the expanded position.

The template tool 120 can optionally include size identifiers 130 configured to identify the radius of each of the openings 126a, 126b, 126c, 126d in the unexpanded position, and hence also a minor axis length of each of the openings 126a, 126b, 126c, 126d. Although the size identifiers 130 representing various sizes are shown as alphabetical characters printed, embossed, or otherwise viewable on the template tool 120, a person skilled in the art will appreciate that the size identifiers 130 can have any size, shape, and configuration, such as any combination of colors or alphabetical, numerical, and symbolic characters.

The template tool 120 can also optionally include size or ruler markings 132 configured to identify the major axis lengths of the openings 126a, 126b, 126c, 126d, e.g., the expanded length $l_{b2}$. The ruler markings 132 can have any size, shape, and configuration, such as about 1 mm spaced tick marks as illustrated. Although the ruler markings 132 are only shown on an elongate bar 134 of the first movable member 122 located between the first and second openings 126a, 126b, a person skilled in the art will appreciate that any of the elongate bars 134 separating any of the openings 126a, 126b, 126c, 126d, and/or any other portion of the first and/or second movable members 122, 124, can include ruler markings. A longitudinal length of the bars 134 can define a maximum major axis length of each of the openings 126a, 126b, 126c, 126d when the template tool 120 is in a fully expanded position, which is illustrated in FIG. 23.

Figure 24:
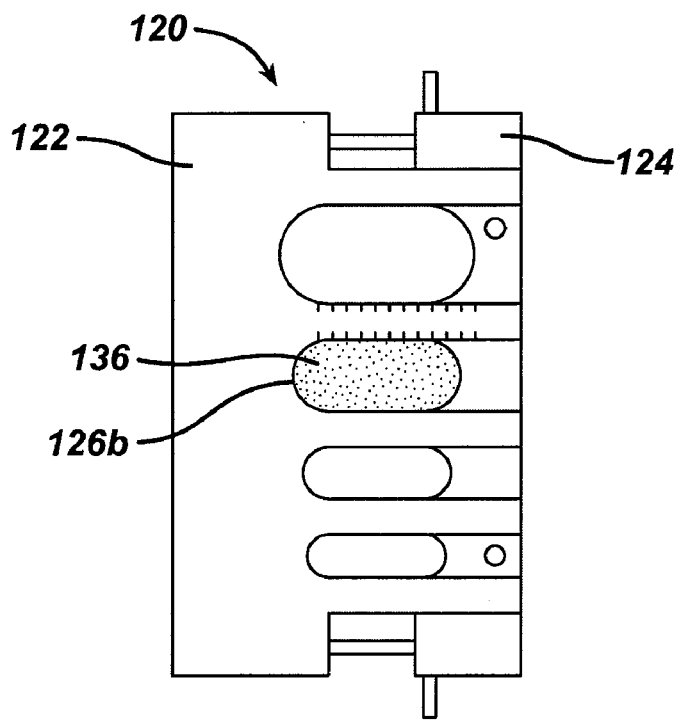
FIG. 24 is a top view of the adjustable template tool of FIG. 23 with tissue scaffold material positioned under at least a portion of the template tool.

In use, the template tool 120 can provide an oblong-shaped opening that can be used to create a desirably sized tissue scaffold. For non-limiting example, if the ovular shape in the tissue shown in FIG. 15 having a minor axis length of double r7 has been created and cleared to form an ovular cavity in the tissue, a major axis length of the ovular shape can be measured, e.g., using the measuring device 112 of FIG. 21. The first and second members of the template tool 120 can be moved such that the one of the openings 126a, 126b, 126c, 126d having a radius equal to the radius r7 in the unexpanded position defines in the expanded position an oblong opening having a major axis length equal to the major axis length of the cavity formed at the defect site 80. A prepared tissue scaffold 136 can be positioned under the template tool 120, as illustrated in an exemplary embodiment in FIG. 24, to at least be positioned under the desirably sized opening, in this embodiment under the second opening 126b. An area of the prepared tissue scaffold 136 having a high concentration of deposited tissue can be positioned under the second opening 126b to help maximize an amount of tissue available in the implant to aid in tissue regeneration. A desirably sized scaffold can be cut in any way from the prepared tissue scaffold 136 using the second opening 126b as a template, as will be appreciated by a person skilled in the art, such as by using a scribing instrument to cut the scaffold 136 around a perimeter of the second opening 126b, or marking the scaffold using the opening 126b and cutting it after removing the template tool 120.

Figure 23:
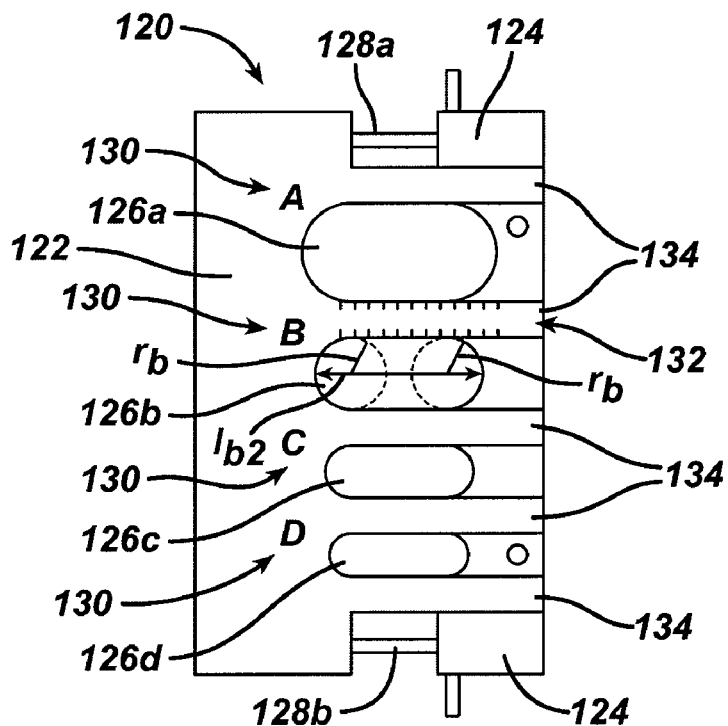
FIG. 23 is a top view of the adjustable template tool of FIG. 22 in an expanded position.

Optionally, the scaffold 136 can be positioned or sandwiched between the template tool 120 and a second template tool similar to the template tool 120 of FIG. 23, which can help make preparing to cut and/or cutting the scaffold 136 an easier, faster process. The two template tools can be independent from one another, or they can be attached together, such as by having their first and second movable members attached together with a space between the tools such that a scaffold can be positioned in the space. The template tools can be fixedly or removably attached to one another, e.g., using alignment pins oriented perpendicular to planes of the tools. When attached, the movable members of the tools can move together.

In another exemplary embodiment using a template tool to help properly size a tissue replacement implant, the template tool can be in the form of a flexible, transparent film. Generally, the flexible, transparent film can be configured to be introduced into a body of a patient adjacent an implant-receiving tissue cavity to help size the cavity. Because the film is transparent, it can be positioned above the cavity to help visualize a size of the cavity through and relative to the film. The film can be removed from the patient's body, trimmed to a visualized size of the cavity, and used as a pattern to cut a tissue replacement scaffold to a desired size. A person skilled in the art will appreciate that the term "transparent" as used herein is intended to include any combination of one or more see-through materials, including optically clear material and translucent material. The film can be any one or more colors, and in an exemplary embodiment, the film is formed of a material in a contrast color such as blue or green that can be easily seen in a body of a patient. While any flexible material can be used to form the film, in an exemplary embodiment the material can be biocompatible and non-malleable such that pressure applied to the film does not substantially deform the film, e.g., the film can substantially return or "spring" to its original, planar configuration after being rolled or having pressure applied thereto as discussed further below. One non-limiting example of a biocompatible and non-malleable material is Ultem™, available from SABIC Innovative Plastics of Pittsfield, Mass. The film can have any thickness configured to allow the film to be introducible to and manipulable within a body of a patient, e.g., about 0.005 inches. (about 0.127 mm).

Figure 25:
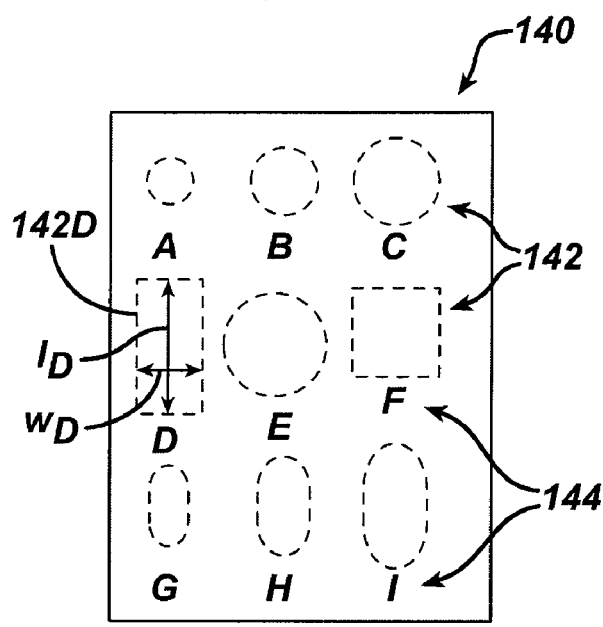
FIG. 25 is a top view of one embodiment of a flexible, transparent film having a plurality of pre-cut shapes formed therein.

As shown in one embodiment in FIG. 25, a flexible, transparent film 140 can include a planar sheet configured to have a least a portion thereof be introduced into a body of a patient. The film 140 can include at least one predefined shape 142, with each of the shapes 142 configured to be removable from the sheet of film 140. The shapes 142 can be removable from the film 140 in a variety of ways, as will be appreciated by a person skilled in the art, such as by having scored perimeter edges configured to allow the shapes 142 to be punched out of the film 140, as illustrated, or having perimeter outlines configured to serve as a guide for a scribing instrument to cut out the shapes 142. When a shape 142 is removed from the film 140, the shape 142 can maintain its planar configuration in a resting position. A person skilled in the art will appreciate that while the film 140 includes nine shapes 142, the film 142 can include any number of shapes. A person skilled in the art will also appreciate that each of the shapes 142 can have a same or different geometric form, e.g., circular, ovular, rectangular, triangular, etc., as any one or more of the other shapes 142. Each of the shapes 142 can include a label 144 configured to identify a shape and/or size of its associated shape 142 to help determine which of the shapes 142 should be chosen to form a template for a given cavity formed in tissue. Although the labels 144 are shown as alphabetical characters printed, embossed, or otherwise viewable on the film 140, a person skilled in the art will appreciate that the labels 144 can have any size, shape, and configuration, such as any combination of colors or alphabetical, numerical, and symbolic characters.

Figure 25A:
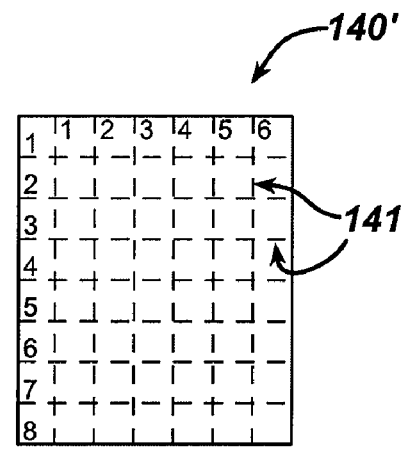
FIG. 25A is a top view of one embodiment of a flexible, transparent film having a plurality of crisscrossing grid lines.

In an alternate embodiment illustrated in FIG. 25A, a flexible, transparent film 140' can include a planar sheet having grid lines 141 printed, embossed, or otherwise viewable on the film 140' that can allow a shape to be cut from the film 140' having a desired shape and size. The grid lines 141 can have uniform spacing, e.g., vertical and horizontal lines about 1 mm apart as shown, similar to graph paper, configured to allow a shape having a particular size to be cut out of the film 140'. The grid lines 141 can also help in estimating a size of a tissue cavity by providing at least one reference point to help in visualizing the cavity relative to the film 140' and trimming the film 140' to a desired size, as discussed further below. The film 140' can be cut in any way, e.g., using a sharp edge of a scribing instrument, as will be appreciated by a person skilled in the art. By allowing a shape to be cut from the film 140' freehand style, the film 140' can provide a greater degree of size and shape choice.

Two or more flexible, transparent films, e.g., the film 140 and/or the film 140', can be provided as part of a kit to help ensure that a film shape is available that can closely match the size of a tissue cavity without requiring a large amount of film trimming, as discussed further below.

Figure 26:
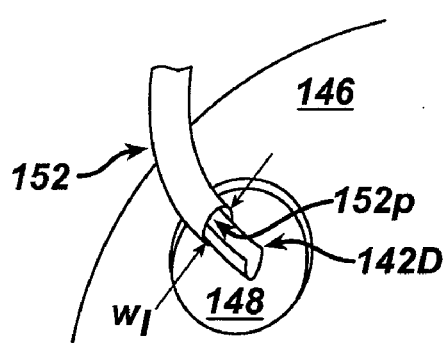
FIG. 26 is a partial perspective view of one embodiment of a flexible, transparent film being advanced through an introducer device to a location adjacent a cavity formed in tissue of a patient.

In use, as shown in one embodiment in FIG. 26, a flexible, transparent film 142D can be introduced into a body of a patient to a site of a cavity 148 formed in cartilage 146 in which a tissue scaffold will be implanted. While the film 142D in this illustrated embodiment includes the rectangular shape 142D removed from the film sheet 140 of FIG. 25, the film 142D can include any one of the shapes 142 punched from the film 140, a shape cut from the gridded film 140', or any other flexible, transparent film. Additionally, while the illustrated cavity 148 is circular-shaped, the film 142D can be used in connection with a cavity having any shape. In an exemplary embodiment the cavity 148 can be formed using a scribing tool as described above, although the film 142D can be used in connection with a cavity formed in any way known in the art or disclosed herein.

The film 142D can be introduced into the patient's body in any way, as will be appreciated by a person skilled in the art. In one embodiment illustrated in FIGS. 26 and 27, the film 142D can be held by a grasper 150 and advanced through a passageway 152p of an introducer device 152, or advanced directly through an opening in tissue, toward a site of the cavity 148. A person skilled in the art will appreciate that the term "grasper" as used herein is intended to encompass any surgical instrument that is configured to grab and/or attach to the film and/or other element and thereby manipulate the film and/or other element, e.g., forceps, retractors, movable jaws, magnets, adhesives, etc. As discussed above, the film 142D can have a planar configuration, but it can be moved to a folded configuration, as shown in FIG. 26, for delivery through the passageway 152p. In this way, the film 142D can be advanced through a passageway having a width $w_t$ that is less than one of, and in an exemplary embodiment both of, the film shape's length $l_D$ and width $w_D$ (see FIG. 25), i.e., a maximum extent. A person skilled in the art will appreciate that the film 142D in the folded configuration can be rolled to have a u-shaped cross-section as shown or can be folded in any other way, e.g., rolled into a cylindrical shape, bent, compressed, etc.

Figure 27:
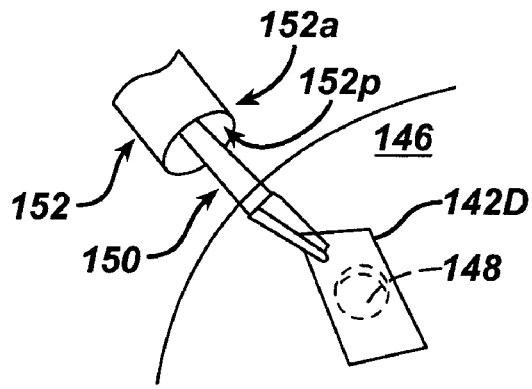
FIG. 27 is a partial perspective view of the film of FIG. 26 positioned over the cavity formed in tissue.

When the film 142D is distally advanced beyond a distal end 152a of the passageway 152p, the film 142D can move from the folded configuration back to its initial, planar configuration, as shown in FIG. 27. As will be appreciated by a person skilled in the art, the film 142D can move from the folded configuration to the planar configuration as the film 142D advances distally beyond the passageway's distal end 152a. The film 142D can be formed from a material that causes the film 142D to automatically move to the planar configuration from the folded configuration, but at least one grasper can optionally be used to grasp and help unfold the film 142D. With the film 142D advanced outside the introducer device 152 and in the planar configuration, the film 152D can be positioned over the cavity 148, as illustrated in FIG. 27. With the film 152D being planar, looking through the film 142D to the cavity 148 positioned underneath the film 142D, e.g., as viewed on a visualization screen outside the patient's body, can allow for a more accurately estimated size of the cavity 148 relative to the film 142D. A perimeter shape of the cavity 148 with respect to the film 142D can be mentally remembered, and/or the film 142D can be physically marked in any way, as will be appreciated by a person skilled in the art, to help in cutting the film 142D to a size and shape substantially matching the size and shape of the cavity 148.

Figure 28:
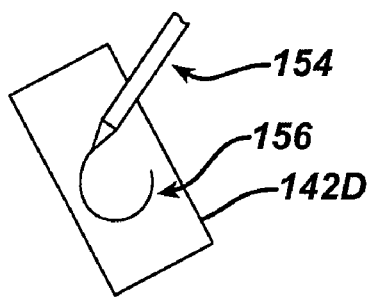
FIG. 28 is a partial perspective view of a shape being cut in the film of FIG. 27 using a scribing instrument.

The film 142D can be trimmed from a size and shape in which it was visually compared with the cavity 148 so the size and shape of the film 142D can more closely match the size and shape of the cavity 148. In an exemplary embodiment, the film 142D can be removed from the patient's body before trimming the film 142D. Trimming the film 142D outside the patient's body to a visualized size and shape of the cavity 148 can help prevent accidental injury to the cartilage 146 or other portion of the patient, can provide for a larger working space, and can help improve accuracy and visualization of cutting of the film 142D. The film 142D can, however, be trimmed to a desired size and shape to match the cavity 148 inside and/or outside the patient's body. The film 142D can be removed from the patient's body in any way, as will be appreciated by a person skilled in the art, such as by being held by the grasper 150 and proximally pulled through the passageway 152p of the introducer device 152. The film 142D can be configured to move from the planar position to the folded position as it is proximally drawn into the passageway 152p in a similar way to how it can be configured to move from the folded position to the planar position, and a grasper can optionally help move the film 142D from the planar configuration to the folded configuration. A person skilled in the art will appreciate that the film 142D can be trimmed in any way, e.g., using a cutting instrument 154 to cut a line 156 in the film 142D, as illustrated in one embodiment shown in FIG. 28. The line 156 in this embodiment forms a circle so the film 142D can be trimmed to approximate the mentally remembered and/or physically marked size and shape of the cavity 148.

Figure 29:
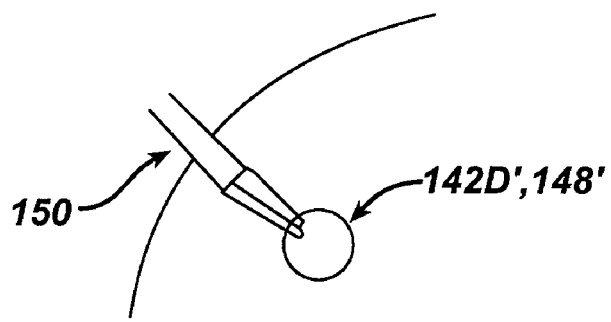
FIG. 29 is a partial perspective view of the film of FIG. 28 positioned over the cavity of FIG. 26.

In one embodiment illustrated in FIG. 29, a trimmed portion 142D' of the film 142D can be introduced into the body of the patient to compare the trimmed film 142D' with the cavity's size and shape. In an exemplary embodiment, the trimmed film 142D' can be introduced into the patient's body the same way that the film 142D was introduced using the introducer device 152 and the grasper 150, but a person skilled in the art will appreciate that the trimmed film 142D' can be inserted in any way into the patient's body, e.g., inserted directly through tissue using a grasper. The trimmed film 142D' can be positioned over the cavity 148 to determine if a size and shape of the trimmed film 142D' substantially matches the cavity's size and shape. The cavity's and trimmed film's sizes and shapes substantially match as illustrated in FIG. 29, so the trimmed film 142D' can be removed from the body in any way and used as a template to cut a tissue scaffold for placement in the cavity 148. If the cavity and trimmed film's sizes and shapes do not substantially match, then the trimmed film 142D' can, similar to that discussed above, be compared with the cavity 148 and re-trimmed inside and/or outside the body. Such comparing and trimming can be repeated as many times as necessary to create a film having a size and shape substantially matching the cavity's size and shape. If the film 142D is trimmed too much and is unacceptably smaller than a size and shape of the cavity 148, the trimmed film 142D' can be discarded and a new flexible, transparent film, e.g., another one of the shapes 142 on the film 140, can be used to begin another process of creating a film template.

Figure 30:
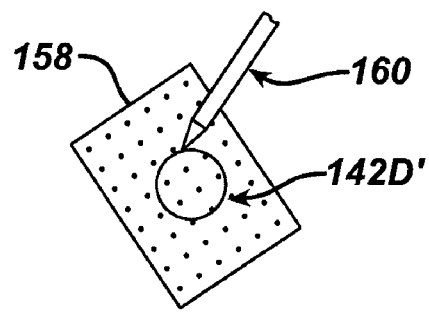
FIG. 30 is a partial perspective view of the film of FIG. 29 positioned over tissue scaffold material, and a scribing instrument cutting the tissue scaffold material using the film as a template.

Once the film 142D has been trimmed to a desired size and shape, if it was trimmed at all, a prepared tissue scaffold 158 can be positioned under the trimmed film 142D', as illustrated in an exemplary embodiment in FIG. 30. An area of the prepared tissue scaffold 158 having a high concentration of deposited tissue can be positioned under the trimmed film 142D' to help maximize an amount of tissue available in the implant to aid in tissue regeneration. A desirably sized scaffold can be cut in any way from the prepared tissue scaffold 158 using the trimmed film 142D' as a template, as will be appreciated by a person skilled in the art, such as by using a cutting instrument 160 to cut the scaffold 158 around a perimeter of the trimmed film 142D'.

Regardless of how a tissue replacement implant is cut to a desired size, the implant can be delivered and affixed to the cavity formed in tissue in any way, as will be appreciated by a person skilled in the art. Non-limiting embodiments of methods and devices for delivering and affixing a tissue replacement implant to tissue can be found in U.S. patent application Ser. No. 12/412,499 entitled "Methods And Devices For Delivering And Affixing Tissue Scaffolds" [Attorney Docket No. 22956-872 (MIT5114USNP)] filed on even date herewith, which is hereby incorporated by reference in its entirety.

The devices discussed herein can be made from any combination of rigid and/or flexible materials, but in an exemplary embodiment the materials are biocompatible. A person skilled in the art will appreciate that the terms "flexible" and "rigid" as used herein are intended to encompass a variety of configurations. Generally, a "flexible" member has some degree of elasticity, e.g., is capable of bending without breaking, while a "rigid" member lacks elasticity. In an exemplary embodiment, the devices or at least portions thereof are composed of at least one biocompatible and flexible material, e.g., plastic, titanium, stainless steel, etc.

A person skilled in the art will appreciate that the present invention has application in conventional endoscopic and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   rotating a scribing device about a longitudinal axis of the scribing device to form a first substantially circular mark in tissue at a defect site;
   rotating a scribing device about a longitudinal axis of the scribing device to form a second substantially circular mark in the tissue at the defect site, the second substantially circular mark partially overlapping the first substantially circular mark; and
   removing tissue within the first and second substantially circular marks to remove a defect in the tissue;
   when removing the tissue within the first and second substantially circular marks comprises removing the tissue within the first and second substantially circular marks down to an outer bone surface underlying the tissue such that a perimeter of a cavity is defined by the first and second substantially circular marks and the outer bone surface forms a bottom of the cavity.

2. The method of claim 1, further comprising forming at least one linear mark in the tissue, the at least one linear mark extending between an outer edge of the first substantially circular mark and an outer edge of the second substantially circular mark.

3. The method of claim 1, further comprising forming first and second linear marks in the tissue, each linear mark being tangent to the first and second substantially circular marks such that the first and second substantially circular marks and the first and second linear marks form an oblong mark in the tissue.

4. The method of claim 1, further comprising implanting a biocompatible tissue repair scaffold in the cavity in the tissue.

5. The method of claim 4, further comprising, prior to implanting the biocompatible tissue repair scaffold, measuring a maximum length of the first and second substantially circular marks formed in the tissue, and cutting the biocompatible tissue repair scaffold to have a size and shape that corresponds to a size and shape of the cavity.

6. The method of claim 5, wherein rotating the scribing device comprises rotating an outer member of the scribing device relative to an inner member of the scribing device that engages bone underlying the tissue.

7. The method of claim 1, wherein the first substantially circular mark has a diameter that differs from a diameter of the second substantially circular mark.

8. The method of claim 1, wherein a first scribing device is used to form the first substantially circular mark and a second scribing device is used to form the second substantially circular mark.

9. The method of claim 1, wherein the tissue is removed from within the first and second substantially circular marks without removing bone underlying the tissue.

10. The method of claim 1, wherein rotating the scribing device comprises rotating an outer member of the scribing device relative to an inner member of the scribing device that engages bone underlying the tissue.

11. A surgical method, comprising:
    advancing a surgical device into a body of a patient to position a distal scribing tip of the device at a defect site in tissue;
    rotating the surgical device about a central longitudinal axis of the surgical device such that the distal scribing tip rotates to form a circular mark in tissue around the defect site;
    removing the tissue within the circular mark to form a circular cavity in the tissue;
    cutting a biocompatible tissue repair scaffold to have a circular shape that corresponds to the circular mark formed in the tissue and that corresponds to a size and a shape of the circular cavity; and
    implanting the biocompatible tissue repair scaffold in the circular cavity in the tissue;
    wherein rotating the surgical device comprises rotating an outer member having the distal scribing tip formed thereon relative to an inner member that engages bone underlying the tissue, and
    wherein removing the tissue within the circular mark to form the circular cavity in the tissue comprises removing the tissue within the circular mark down to an outer bone surface underlying the tissue such that a perimeter of the cavity is defined by the circular mark and the outer bone surface forms a bottom of the cavity.

12. The method of claim 11, wherein the surgical device is inserted through an opening in tissue, and wherein the circular mark has a diameter that is greater than a diameter of the opening.

13. The method of claim 11, wherein cutting the biocompatible tissue repair scaffold comprises punching the scaffold with a punch having a diameter that corresponds to a diameter of the circular mark formed in the tissue.

14. The method of claim 11, wherein the circular mark has a diameter in the range of about 5 to 40 mm.

15. The method of claim 11, wherein the biocompatible tissue repair scaffold has a viable tissue disposed thereon.

16. The method of claim 11, wherein implanting the biocompatible tissue repair scaffold comprises positioning an outer surface of the biocompatible tissue repair scaffold against the outer bone surface forming the bottom of the cavity.

17. The method of claim 11, wherein the biocompatible tissue repair scaffold is cut to have the circular shape using the distal scribing tip of the device.

18. The method of claim 11, wherein the inner member engages the outer bone surface and the distal scribing tip forms the circular mark in the tissue without significantly cutting the bone.

19. The method of claim 11, wherein cutting the biocompatible tissue repair scaffold comprises rotating the outer member having the distal scribing tip formed thereon relative to the inner member that engages material forming the biocompatible tissue repair scaffold.

20. The method of claim 11, further comprising advancing the inner member through an inner passageway extending through the outer member.

* * * * *